United States Patent
Bi et al.

(10) Patent No.: US 11,634,552 B2
(45) Date of Patent: Apr. 25, 2023

(54) ORGANIC AMINE SALT FOAMER

(71) Applicant: Shandong University of Technology, Shandong (CN)

(72) Inventors: Gehua Bi, Shandong (CN); Yusui Bi, Shandong (CN)

(73) Assignee: Shandong University of Technology, Shandong (CN)

( * ) Notice: Subject to any disclaimer, the term of this patent is extended or adjusted under 35 U.S.C. 154(b) by 458 days.

(21) Appl. No.: 16/753,064

(22) PCT Filed: Dec. 5, 2017

(86) PCT No.: PCT/CN2017/114589
§ 371 (c)(1),
(2) Date: Apr. 2, 2020

(87) PCT Pub. No.: WO2019/075875
PCT Pub. Date: Apr. 25, 2019

(65) Prior Publication Data
US 2020/0291199 A1    Sep. 17, 2020

(30) Foreign Application Priority Data
Oct. 19, 2017    (CN) .......................... 201710980334.3

(51) Int. Cl.
*C08J 9/08*      (2006.01)
*C07C 213/08*    (2006.01)
(Continued)

(52) U.S. Cl.
CPC ............... *C08J 9/08* (2013.01); *C07C 213/08* (2013.01); *C08J 9/146* (2013.01); *C07C 215/06* (2013.01);
(Continued)

(58) Field of Classification Search
CPC . C08J 9/08; C08J 9/146; C08J 2203/02; C08J 2203/06; C08J 2203/142;
(Continued)

(56) References Cited

U.S. PATENT DOCUMENTS 2,399,142 A * 4/1946 Reed .................. B01D 53/1425
                                                          423/563
4,542,214 A * 9/1985 Bechara ............. C08G 18/1875
                                                          548/335.1
(Continued)

FOREIGN PATENT DOCUMENTS

CN       105601978 A *  5/2016
CN       105601978 A    5/2016
(Continued)

OTHER PUBLICATIONS

International Search Report (PCT/ISA/210) dated Jun. 4, 2018, by the State Intellectual Property Office of the P.R. China Patent Office as the International Searching Authority for International Application No. PCT/CN2017/114589 (English Translation).
(Continued)

*Primary Examiner* — Kara B Boyle

(57) ABSTRACT

Disclosed is an organic amine salt foaming agent, that is, a composite polyurethane foaming agent, comprising: 1) hexafluorobutene; and 2) an alkanolamine salt mixture (MAA), the alkanolamine salt mixture (MAA) contains an organic amine salt compound having the following general formula (I): $A^{n-}[B^{m+}]_p$ (I); wherein $A^{n-}$ is one or two or three selected from the following anions: (b) carbonate: $CO_3^{2-}$; (c) formate: $HCOO^-$; (d) bicarbonate: $HO-COO^-$. A polyurethane foaming method using carbon dioxide and an organic amine in combination is also disclosed, in which carbon dioxide is added to a polyurethane composition for foaming. A method for preparing an alkanolamine carbonate salt with low water content from ammonium carbonate and
(Continued)

an epoxide is additionally disclosed, in which a liquid alkanolamine salt mixture is used as a dispersion medium or as a solvent for reaction raw material.

16 Claims, 1 Drawing Sheet

(51) Int. Cl.
  *C08J 9/14* (2006.01)
  *C07C 215/06* (2006.01)
(52) U.S. Cl.
  CPC ........ *C08J 2203/02* (2013.01); *C08J 2203/06* (2013.01); *C08J 2203/142* (2013.01); *C08J 2203/164* (2013.01); *C08J 2203/182* (2013.01); *C08J 2203/184* (2013.01); *C08J 2375/06* (2013.01); *C08J 2375/08* (2013.01)
(58) Field of Classification Search
  CPC ............ C08J 2203/164; C08J 2203/182; C08J 2203/184; C08J 2375/06; C08J 2375/08; C08J 9/0028; C08J 9/10; C08J 9/122; C08J 2203/08; C08J 2203/162; C08J 2375/04; C08J 2203/204; C08J 2203/04; C08J 2203/10; C08J 9/04; C08J 9/104; C08J 9/125; C07C 213/08; C07C 215/06; C07C 241/02; C07C 243/14; C08G 2110/0025; C08G 18/163; C08G 18/1816; C08G 18/2063; C08G 18/225; C08G 18/3271; C08G 18/3275; C08G 18/4018; C08G 18/42; C08G 18/482; C08G 18/5027; C08G 18/6688; C08G 18/7664; C08G 18/10
  See application file for complete search history.

(56) References Cited

U.S. PATENT DOCUMENTS

| | | | |
|---|---|---|---|
| 2012/0041088 A1* | 2/2012 | Ishida | ................ C08G 18/3265 516/15 |
| 2019/0016673 A1 | 1/2019 | Bi et al. | |
| 2019/0152899 A1 | 5/2019 | Bi et al. | |

FOREIGN PATENT DOCUMENTS

| | | |
|---|---|---|
| CN | 10709910 A | 8/2017 |
| CN | 107089916 A | 8/2017 |
| CN | 107089927 A | 8/2017 |
| CN | 107253919 A | 10/2017 |

OTHER PUBLICATIONS

Written Opinion (PCT/ISA/237) dated Jun. 4, 2018, by the State Intellectual Property Office of the P.R. China Patent Office as the International Searching Authority for International Application No. PCT/CN2017/114589.

* cited by examiner

ORGANIC AMINE SALT FOAMER

RELATED APPLICATION

This application is a U.S. National Phase application of International Patent Application No. PCT/CN2017/114589, filed Dec. 5, 2017. The disclosure of which is herein incorporated by reference in its entirety.

FIELD OF THE INVENTION

The present invention relates to a composite foaming agent containing hexafluorobutene and an organic alkanolamine salt compound, and its application in foaming materials such as polyurethane foam or PVC foam or polystyrene foam. The invention also relates to a polyurethane foaming method using carbon dioxide and organic amines in combination, which uses gaseous carbon dioxide, liquid carbon dioxide and/or supercritical carbon dioxide as foaming agents, and belongs to the field of polyurethane foam materials. The invention also relates to a method for preparing a low water content alkanolamine carbonate salt, and more particularly, to a method for recycling and preparing a low water content alkanolamine carbonate salt.

BACKGROUND OF THE INVENTION

Polyurethane rigid foam, as a new polymer material, has light weight, high strength and extremely low thermal conductivity. It is a high-quality thermal insulation material, and widely used in refrigerated insulation, especially chemical weapons refrigerated insulation, building energy saving, solar energy automobiles, refrigerators, freezers and other home appliances and other industries. The most important raw material in the production of rigid polyurethane foam is the foaming agent. At present, all of these blowing agents are chlorofluorocarbons except cyclopentane. Due to their damage to the atmospheric ozone layer, governments have already signed the international convention of the "Montreal Agreement" to restrict and phase out the production and use of such products. China is also a signatory of the agreement.

At present, China is still using the second-generation chlorofluorocarbon blowing agent HCFC-141b (monofluorodichloroethane) and cyclopentane. Developed countries in Europe and the United States have already banned the use of HCFC-141b. In China, the consumption of HCFC-141b will be frozen at the consumption levels of 2009 and 2010, and 20% of the frozen consumption will be phased out in 2015, and it is promised to completely ban production and use of it by 2025. At present, the developed countries in Europe and the United States use the third-generation foaming agents pentafluoropropane (HFC-245fa) and pentafluorobutane (HFC-365), but the second and third-generation foaming agents have high GWP (greenhouse effect potential), which seriously damages the atmospheric ozone layer, so Europe and the United States will ban the use of third-generation foaming agents by 2017. For this reason, Honeywell Corporation in the United States has developed the fourth-generation physical blowing agent chlorotrifluoropropylene (LBA), although the ODP (potential damage to the ozone layer) is zero and relatively environmentally friendly than the third generation, this product is expensive, and the GWP is still higher. In short, these physical blowing agents other than cyclopentane are the culprits of damaging the ozone layer in the atmosphere, because they all contain chlorofluorine and will be eliminated.

It is disclosed in the prior art that $CO_2$ is directly used as a polyurethane foaming agent; however, due to the escape of $CO_2$ gas and its poor solubility in raw materials MDI and polyester polyols and/or polyether polyols, $CO_2$ gas cannot be uniformly dispersed in a foaming composition, and the foaming process is not easy to control.

In addition, it is disclosed in the prior art that a small amount of water is directly used as a polyurethane foaming agent. However, in view of the hydrogen bonding effect of water molecules and the poor solubility of water in polyester polyols and/or polyether polyols, water molecules are present in the form of microdroplets in a foaming composition such as polyether polyol components, causing local excessive reaction and foaming in the foaming material. If water is solely used as the blowing agent, more urea bonds will be contained in the polyurethane foam material, which greatly affects the strength and thermal insulation performance of the foam material. In addition, if the amount of water used as the foaming agent is slightly increased, it will significantly affect the performance and dimensional stability of a polyurethane foam. If water is used as the sole blowing agent, a polyurethane foam suffer from shrinkage, scorch, and inadequate heat insulation.

In short, foaming agents in the prior art cannot be dispersed in a foaming composition at the molecular level, which causes uneven distribution of the cells and uneven size of the cells, and ultimately affects the strength properties and thermal insulation of the resulting foam.

In addition, hexafluorobutene (boiling point is about 33° C., trade name FEA-1100) is used as a polyurethane foaming agent in the prior art, however, its production cost and sales price are high, and polyurethane foam prepared by using it as a foaming agent is still inadequate in performance, especially the thermal insulation performance is significantly reduced and deformed at low or ultra low temperature conditions (because the foaming agent becomes a liquid, the vapor pressure in the cells becomes lower, and the phenomenon of collapse is very serious.

In addition, it discloses in the prior art a method for preparing polyurethane foam using liquid $CO_2$ foaming or supercritical carbon dioxide foaming, wherein $CO_2$ or supercritical carbon dioxide is directly used as a polyurethane foaming agent. In view of the fact that $CO_2$ gas is a natural gas in the atmosphere, non-combustible, non-toxic and environmentally friendly, this is a very environmentally friendly and safe foaming technology. However, due to the escape of $CO_2$ gas and its low solubility in raw materials MDI and polyester polyols and/or polyether polyols, it must use ultra-high operating pressure of liquid $CO_2$ in order to increase the dissolved amount of $CO_2$ in the above raw materials to meet foaming requirements. In general, the operating pressure of liquid $CO_2$ is higher than 25 MPa, which imposes a high requirement on the equipment and is not convenient for practical industrial production applications, and the foaming process is difficult to control. In addition, considering the poor solubility of $CO_2$ gas in a foaming composition, most of $CO_2$ gas cannot be uniformly dispersed in the foaming composition, resulting in uneven distribution of cells and uneven size of the cells, which ultimately affect the strength properties and thermal insulation properties of foamed materials.

Chinese patent publication application 201610393108.0 discloses an alkanolamine carbonate amine salt and a preparation method thereof. However, the resulting alkanolamine carbonate product still has a relatively high water content, and it is impossible to remove water by distillation or vacuum evaporation, because its decomposition temperature is around 60° C., and $CO_2$ is removed from polyurethane molecule at the same time in the process of removing water. However, how to prepare an alkanolamine carbonate with a low water content is still a difficulty in the art.

SUMMARY OF THE INVENTION

In order to overcome the shortcomings in the prior art, the object of the present invention is to provide a composite foaming agent for a polyurethane foam material.

The inventors of the present application unexpectedly found that, when hexafluorobutene is combined with an organic alkanolamine salt mixture (MAA) as a polyurethane blowing agent, the obtained polyurethane foam material not only has better thermal insulation property, and has good deformation resistance and thermal insulation at low or ultra-low temperature, which is of great significance for the application of polyurethane foam in the field of cryogenics.

According to a first embodiment of the present invention, a composite foaming agent (i.e., a composite foaming agent comprising hexafluorobutene and organic alkanolamine salt compound) is provided, comprising:

1) hexafluorobutene; and
2) an alkanolamine salt mixture (MAA), the organic alkanolamine salt mixture (MAA) comprises an organic alkanolamine salt compound, and the organic alkanolamine salt compound has following general formula (I):

$$A^{n-}[B^{m+}]_p \quad (I)$$

wherein $A^{n-}$ is a $CO_2$-donating anion with a valence of −n, wherein n=1, or 2;

$B^{m+}$ comprises or each $B^{m+}$ is independently: ammonium ion of +1 valence ($^+NH_4$), hydrazinium ion of +1 valence ($H3^+N-NH_2$), hydrazinium ion of +2 valence ($H_3^+N-NH_3^+$), and/or, one or more organic amine (B) cation(s) having m of $-^+NR^3R^4H$ groups and/or $-^+NR^3H-$ groups; wherein m=1-5;

$$0 < p \le \frac{n}{m};$$

and wherein $A^{n-}$ is one or two or three selected from a group consisting of following anions:
(b) carbonate: $CO_3^{2-}$;
(c) formate: $HCOO^-$;
(d) bicarbonate: $HO-COO^-$;

wherein $R^3$ or $R^4$ is independently chosen from: H, R, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;

provided that: the compound of the general formula (I) has at least one (for example one or two) R group(s) linked to N atom (i.e., N—R group), and the alkanolamine salt mixture (MAA) contains 50-99 wt % (the balance is water and optional impurities) of monoalkanolamine (for example monoethanolamine and/or monoisopropanolamine) salt or dialkanolamine (for example diethanolamine, ethanol isopropanol amine and/or di-isopropanolamine) salt, based on total weight of the alkanolamine salt mixture (MAA);

wherein the R group is one or more selected from following groups:
(1a) $H[OCH(R_{1a})CH(R_{2a})]_q-$;
(2a) $H[OCH(R_{1a})CH(R_{2a})CH(R_{3a})]_q-$; or
(3a) $H[OCH(R_{1a})CH(R_{2a})CH(R_{3a})CH(R_{4a})]_q-$;

wherein the value or average value of q is q=1-3 (for example 2); $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;

wherein the water content in the alkanolamine salt mixture (MAA) is from more than 0 wt % to 40 wt %, and said organic amine compound (B) is an organic amine compound (B) having 2-50 carbon atoms;

wherein the weight ratio of the hexafluorobutene to the alkanolamine salt mixture (MAA) in the composite blowing agent is 0.1-10:1.

Preferably, $A^{n-}$ is (b) carbonate: $CO_3^{2-}$; or, $A^{n-}$ is a combination or mixture of (b) carbonate ($CO_3^{2-}$) with (c) formate ($HCOO^-$) and/or (d) bicarbonate ($HO-COO^-$).

Preferably, in the composite foaming agent, (1a) $H[OCH(R_{1a})CH(R_{2a})]_q-$ is $H(OCH_2CH_2)_q-$, $H(OCH_2CH(CH_3))_q-$, $H(OCH(CH_3)CH_2)_q-$, $H(OCH_2CH(C_6H_5))_q-$, $H(OCH(C_6H_5)CH_2)_q-$, $H(OCH_2CH(CH_2Cl))_q-$, $H(OCH(CH_2Cl)CH_2)_q-$ or $H(OCH_2CH(CBr_3))_q-$.

Preferably, the weight ratio of hexafluorobutene to the alkanolamine salt mixture (MAA) in the composite blowing agent is 0.2-5:1, more preferably 0.3-4:1, more preferably 0.4-3:1, more preferably 0.5-2:1, more preferably 0.7-1.3:1.

Preferably, the content of water in the alkanolamine salt mixture (MAA) is 5-35 wt %, preferably 10-30 wt %, and more preferably 15-25 wt %.

Preferably, the alkanolamine salt mixture (MAA) contains 60-98 wt %, preferably 70-97 wt %, and more preferably 80-96 wt % of a monoalkanolamine (such as monoethanolamine and/or monoisopropanolamine) salt and a dialkanolamine (e.g. di-ethanolamine, ethanol propanolamine, and/or dipropanolamine) salt.

In the present application, the monoalkanolamine salt is, for example, ammonium ethanolamine carbonate, or bis(ethanolamine) carbonate. In the present application, the di-alkanolamine is, for example, ammonium (diethanolamine) carbonate, (ethanolamine) (diethanolamine) carbonate, or bis(diethanolamine) carbonate.

Preferably, the pH of the alkanolamine salt mixture (MAA) is 7.5-10, preferably 7.8-9.5, and more preferably 8-9.0.

Preferably, in the alkanolamine salt mixture (MAA), the total content of the compound of the general formula (I) (that is, the organic alkanolamine salt compound) and water is 70-100%, preferably 80-99.5%, more preferably 85-99.0%, based on the total weight of the alkanolamine salt mixture (MAA).

Preferably, the organic alkanolamine salt compound is a salt formed from monoalkanolamine (such as monoethanolamine and/or monopropanolamine) and/or a di-alkanolamine (such as diethanolamine, ethanol propanol amine, and/or di-propanolamine) and an anion, the anion is one or two or three selected from the following anions:
(b) carbonate: $CO_3^{2-}$;
(c) formate: $HCOO^-$;
(d) bicarbonate: $HO-COO^-$.

Herein, the monoalkanolamine and/or dialkanolamine is referred to: a monoalkanolamine, a di-alkanolamine, or a mixture of a monoalkanolamine and a di-alkanolamine.

Preferably, the above-mentioned alkanolamine salt mixture (MAA) is obtained by reaction of the first raw material and the second raw material in the presence of water (preferably, the amount of water is 70-250 wt %, preferably 85-200 wt %, more preferably 100-170 wt %, more preferably 110-160 wt %, based on the weight of the first raw material), optionally in the presence of a catalyst; wherein the first raw material is one or more (for example, two or three) selected from the following compounds:

$H_2N$—$COONH_4$;

$(NH_4)_2CO_3$, hydrazinium carbonate, ammonium hydrazinium carbonate, or organic amine compound (M) carbonate;

$HCOONH_4$, hydrazinium formate, or organic amine compound (M) formate;

HO—$COONH_4$, hydrazinium bicarbonate, or bicarbonate of organic amine compound (M);

the second raw material is one or more (e.g., two or three) selected from the following epoxides:

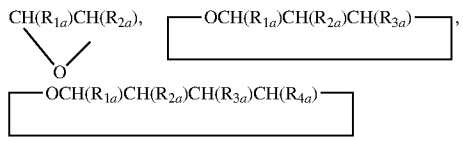

or styrene oxide; wherein $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;

wherein the organic amine compound (M) is an organic amine compound selected from following compounds:

$C_1$-$C_{24}$ hydrocarbyl amines;

Di-($C_1$-$C_{16}$ hydrocarbyl) amines;

$C_2$-$C_{14}$ hydrocarbylene diamines;

$C_4$-$C_{16}$ polyalkylene polyamines;

$C_3$-$C_{18}$ organic triamines having three primary amine groups or $C_5$-$C_{18}$ organic tetramines having four primary amine groups; or $C_2$-$C_{10}$ alkanolamines.

Preferably, in the present application, the organic amine compound (B) is an organic amine compound having N—R group(s), and the organic amine compound (B) having N—R group(s) is formed by the organic amine compound (M), or ammonia being substituted on its at least one N atoms by one or more of above-mentioned R groups, wherein the definition of R group is defined as above.

Preferably, q=1-2.5, more preferably q=1-2.0, calculated as the average value of q.

In general, the organic amine (B) has from m to m+3 of primary amine, secondary amine and/or tertiary amine groups, and optionally has quaternary ammonium group.

Preferably, said organic amine compound (B) is an organic amine compound having 2-20 carbon atoms.

Preferably, $B^{m+}$ is a combination or mixture of two or more of above-mentioned organic amine cations.

Preferably, said organic amine compound (B) is an organic amine compound having 3-12 carbon atoms.

Preferably, $R^3$ or $R^4$ is independently chosen from: H, R, $C_1$-$C_4$ aliphatic hydrocarbyl group optionally substituted by hydroxyl or amino or halogen, cyclobutyl or cyclohexyl optionally substituted by hydroxyl or amino or halogen, or phenyl or methylphenyl optionally substituted by hydroxyl or amino or halogen; and also, $R_{1a}$, $R_{2a}$, $R_{3a}$ or $R_{4a}$ each independently is selected from the following groups: H, methyl, or ethyl optionally substituted by hydroxyl or amino or halogen, propyl or isopropyl optionally substituted by hydroxyl or amino or halogen, cyclohexyl optionally substituted by hydroxyl or amino or halogen, or, phenyl or methylphenyl optionally substituted by hydroxyl or amino or halogen.

Preferably, $R_{1a}$, $R_{2a}$, $R_{3a}$ or $R_{4a}$ each independently is selected from the following groups: H, methyl, chloromethyl, bromomethyl, ethyl, cyclohexyl, or phenyl.

Preferably, the mass content of alkali metals and alkaline earth metals in the composite foaming agent is 0-200 ppm.

Preferably, the compound of the general formula (I) contains an average of 1.3-5 of R groups per molecule, such as 1.4-4 (e.g. 3) of R groups, preferably 1.5-2 of R groups.

Preferably, the epoxide is: ethylene oxide, propylene oxide, epichlorohydrin, bromopropylene oxide, butylene oxide, epoxy chlorobutane or styrene oxide, or a mixture of any two or more of them.

The above catalyst is aqueous ammonia.

According to a second embodiment of the present invention, there is also provided a polyurethane foaming composition comprising:

0.1-100 wt %, preferably 1-80 wt %, more preferably 3-60 wt % (for example, 10 wt %, 15 wt %, 20 wt %, 30 wt %, 40 wt %, 50 wt %) of the composite blowing agent described above;

0-50 wt %, preferably 0-40 wt %, more preferably 0.2-30 wt % (e.g., 0.5 wt %, 1.0 wt %, 1.5 wt %, 2.0 wt %, 5 wt %, 10 wt %, or 20 wt %) of physical blowing agents other than hexafluorobutene;

0-6 wt %, preferably 0.5-5 wt %, more preferably 0.7-4 wt % water, and 0.0-99.9 wt %, preferably 20.0-99 wt %, more preferably 40-97 wt % (for example, 90 wt %, 85 wt %, 80 wt %, 70 wt %, 60 wt %, 50 wt %) of a polymer polyol; wherein the weight percentages are based on the total weight of the polyurethane foam composition.

In addition, according to a third embodiment of the present invention, a composition for preparing polyurethane foam material is also provided, which comprises:

0.1-10 wt %, preferably 0.3-8 wt %, more preferably 0.5-6 wt % of hexafluorobutene;

0.2-90 wt %, preferably 1-80 wt %, more preferably 3-70 wt % of an organic alkanolamine salt compound;

0-50 wt %, preferably 0.2-40 wt %, more preferably 0.5-30 wt % of physical blowing agents other than hexafluorobutene;

0.1-10 wt %, preferably 0.3-9 wt %, more preferably 0.5-8 wt % of water, and 0.0-99.6 wt %, preferably 20.0-98.2 wt %, more preferably 40-96.5 wt % of a polymer polyol; wherein the weight percentage is based on the total weight of the polyurethane foaming composition;

wherein the organic alkanolamine salt compound is an organic amine salt compound having the following general formula (I):

$$A^{n-}[B^{m+}]_p \quad (I)$$

in the above formula, $A^{n-}$ is an anion with −n valence as a $CO_2$ donor, where n=1 or 2;

$B^{m+}$ comprises or each $B^{m+}$ is independently: ammonium ion of +1 valence ($^+NH_4$), hydrazinium ion of +1 valence ($H_3^+N$—$NH_2$), hydrazinium ion of +2 valence ($H_3^+N$—$NH_3^+$), and/or, one or more organic amine (B) cation(s) having m of —$^+NR^3R^4H$ groups and/or —$^+NR^3H$— groups;

wherein m=1-5;

$$0 < p \le \frac{n}{m};$$

and
wherein $A^{n-}$ is one or two or three selected from a group consisting of following anions:
(b) carbonate: $CO_3^{2-}$;
(c) formate: $HCOO^-$;
(d) bicarbonate: $HO-COO^-$;
wherein $R^3$ or $R^4$ is independently chosen from: H, R, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;
provided that: the compound of the general formula (I) has at least one (e.g one or two) R groups linked to N atom, i.e., —N—R group(s);
wherein the R group is one or more groups selected from following groups:
(1a) $H[OCH(R_{1a})CH(R_{2a})]_q$—;
(2a) $H[OCH(R_{1a})CH(R_{2a})CH(R_{3a})]_q$—; or
(3a) $H[OCH(R_{1a})CH(R_{2a})CH(R_{3a})CH(R_{4a})]_q$—;
wherein the value or average value of q is q=1-3 (e.g., 2); $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;
wherein said organic amine compound (B) is an organic amine compound having 2-50 carbon atoms;
Preferably, the organic alkanolamine salt compound is a salt formed from a monoalkanolamine (eg, monoethanolamine and/or monopropanolamine) and/or a di-alkanol amine (eg, diethanolamine, ethanolpropanolamine, and/or dipropanolamine) and an anion, wherein the anion is one or two or three selected from the following anions:
(b) carbonate: $CO_3^{2-}$;
(c) formate: $HCOO^-$;
(d) bicarbonate: $HO-COO^-$.
Preferably, the organic alkanolamine salt compound contains 50-100 wt % (60-98 wt %, preferably 70-96 wt %, more preferably 80-94 wt %) of a salt of monoalkanolamine (such as monoethanolamine and/or monopropanolamine) and a salt of di-alkanolamine (such as diethanolamine, ethanolpropanolamine, and/or dipropanolamine), based on the total weight of the organic alkanolamine salt compound.
Preferably, the weight ratio of hexafluorobutene to the organic alkanolamine salt compound in the polyurethane foaming composition is 0.2-5:1, more preferably 0.3-4:1, more preferably 0.4-3:1, more preferably 0.5-2:1, more preferably 0.7-1.3:1.
Preferably, the polyurethane foaming composition contains, in all, 0.2-8 wt %, 0.4-6 wt %, 0.5-5 wt %, preferably 0.7-4 wt %, more preferably 1-3 wt % of water.
Preferably, the foaming composition further comprises: foam stabilizer, catalyst and flame retardant et al. These auxiliaries often are used in the field of polyurethane.
In the present application, propanolamine includes: 3-hydroxypropylamine, 2-hydroxypropylamine (ie, isopropanolamine), and/or 2-aminopropanol.
Preferably, the polymer polyol is selected from: polyether polyol, polyester polyol, polyether-polyester polyol, polycarbonate diol, polycarbonate-polyester polyol, polycarbonate-polyether polyol, polybutadiene polyol or polysiloxane polyol. The average functionalities of the polymer polyol is in general 2-16, preferably 2.5-10, more preferably 3-8. Preferably, the polymer polyol is a combination of polyether polyols.
Preferably, the physical foaming agent is at least one selected from: n-pentane, isopentane, cyclopentane, other alkanes having a boiling point in a range of 0-100° C., HCFC-141b, HFC-245fa, HFC-365mfc, LBA, other fluorochlorohydrocarbons having a boiling point in a range of 0-100° C., and methyl formate.
According to a fourth embodiment of the present invention, a polyurethane foam material is provided, which is formed by the mixing and reacting of above-mentioned polyurethane foaming composition with polyisocyanate monomer, isocyanate terminated prepolymer, or a mixture of polyisocyanate monomer and isocyanate terminated prepolymer.
The decomposition temperature of the compound(s) of the general formula (I) of present invention is in general in a range of 45-120° C., preferably 50-70° C., or is in a range of 45-70° C. when it comes into contact with isocyanate.
In the present application, the alkanolamine salt mixture (MAA) is used interchangeably with the compound or compound mixture of the general formula (I).
In addition, according to a fifth embodiment of the present invention, a polyurethane foaming method using carbon dioxide and organic amines is provided.
In order to overcome the shortcomings in the prior art, the object of the present invention is to provide a new polyurethane foaming technology, which improves the traditional liquid $CO_2$ foaming technology, and improves problems in the traditional liquid $CO_2$ foaming process, such as excessive equipment pressure, unevenness of cells distribution and non-uniform cell size. Because, on the one hand, the miscibility between $CO_2$ and the polymer polyol or isocyanate is not good, and thus it is difficult for $CO_2$ to be uniformly dispersed in the starting material for foaming. In particular, on the other hand, when a $CO_2$ foaming process is used, a high-pressure mixer is often used, and for example, the pressure reaches 4-7 MPa during mixing, so uniform mixing cannot be achieved by stirring under high pressure.
The present invention relates to the use of organic amine compounds or mixtures thereof, as $CO_2$ solubilizers and also as catalysts, cross-linking agents or chain extenders, in the polyurethane foaming process using liquid $CO_2$, and in the preparation of foam materials such as polyurethane refrigerator and freezer foam materials, polyurethane intermittent-plate foam materials, polyurethane continuous-plate foam materials, polyurethane spray-coated foam materials, polyurethane solar-energy foam materials.
In the foaming technology involved in the present invention, because organic amines (OA) are added as a solubilizing agent to the polyurethane foaming composition, and the solubility of $CO_2$ in the foaming composition is significantly improved, so when gaseous $CO_2$ foaming technology is used, in particular, when the liquid $CO_2$ foaming technology is used for foaming, the homogeneous mixing of the foaming composition and $CO_2$ can be achieved by using lower operating pressure conditions, so as to meet the foaming demand. The inventors of the present application have unexpectedly discovered that the organic amine in the composition reacts with most of the $CO_2$ dissolved in the composition under the condition of liquid $CO_2$ to form an organic amine-$CO_2$ adduct, and the above-mentioned adduct is easy to decompose under elevated temperature condition to produce $CO_2$ gas, and even when foaming is performed at a lower temperature, the above-mentioned adduct can be activated by the NCO groups contained in isocyanate monomers such as MDI and TDI to quickly release $CO_2$ gas. In addition, due to the formation of the above-mentioned adducts, most of the $CO_2$ can be fully dissolved in the foaming composition (such as polyether polyol or polyester polyol) or have good miscibility with the foaming composition, so that, in the foaming technology of the present invention, $CO_2$ can be uniformly dispersed in the foaming composition for uniform foaming; especially when the organic amine is uniformly mixed in the white material before the white material and the black material are mixed and foamed, $CO_2$ can be uniformly mixed and dispersed in the white material without stirring under high pressure. Therefore, the distribution of the cells in the prepared polyurethane foam is relatively uniform, and the size of the cells is relatively uniform. In addition, after the organic amine-$CO_2$ adduct of the present invention decomposes and releases $CO_2$, the resultant decomposition product is an organic amine compound, which is suitable as a polyurethane cross-linking agent, a chain extender, and a catalyst for use in foaming materials, and which not only improves the strength and dimensional stability of the resulting foam, but also reduces the use amount of other catalysts. In particular, when an alkanolamine is used as the organic amine, the prepared polyurethane foam material has excellent deformation resistance and excellent thermal insulation properties under cryogenic conditions. Therefore, the present invention has been accomplished based on the above aspects.

In the present application, "organic amine as a $CO_2$ solubilizer" refers to an organic amine that can form an adduct with $CO_2$ under the condition of liquid $CO_2$ to improve the solubility of $CO_2$ in the composition.

According to the present invention, there is provided a polyurethane foaming method using carbon dioxide and an organic amine in combination, comprising: a polyurethane foaming composition (referred to as a "white material") and a polyisocyanate monomer and/or an isocyanate-terminated isocyanate prepolymer (referred to as "black materials") are separately conveyed as separate material streams (preferably, continuously) to a mixer (preferably a pressure mixer) for mixing and then the resulting mixture is foamed; wherein, carbon dioxide (e.g. under pressure) is added (preferably, continuously) to the polyurethane foaming composition (ie "white material") or to the polyisocyanate monomer and/or isocyanate-terminated prepolymer (ie "black material") or simultaneously to the polyurethane foaming composition and the polyisocyanate monomer and/or isocyanate-terminated prepolymers, before the two material streams (i.e. white material and black material) enter (e.g. continuously) to the mixer for mixing (or before the two material streams are transported into the mixer); and wherein carbon dioxide is gaseous carbon dioxide, liquid carbon dioxide, subcritical carbon dioxide and/or supercritical carbon dioxide [i.e., wherein the carbon dioxide is one or more selected from gaseous carbon dioxide, liquid carbon dioxide, subcritical carbon dioxide or supercritical carbon dioxide];

the polyurethane foaming composition comprises:
60.0-99.0 wt %, preferably 70.0-96 wt %, more preferably 80-95 wt % (e.g. 85 wt %) of a polymer polyol,
1 to 40 wt %, preferably 2 to 35 wt %, preferably 3 to 30 wt %, and more preferably 5 to 20 wt % (for example, 7 wt %, 12 wt %, or 15 wt %) of organic amines (OA),
0-50 wt %, preferably 0-40 wt %, more preferably 0-30 wt % of physical blowing agents other than carbon dioxide,
0-8 wt %, preferably 0.3-6 wt %, more preferably 0.5-5 wt %, more preferably 0.7-4 wt % water, and
0-8 wt %, preferably 0.5-6 wt %, more preferably 1-5 wt % of ammonia and/or hydrazine, wherein, the weight percentage is based on the total weight of the polyurethane foaming composition.

In this application, "optionally" means carrying out or not carrying out.

As described therein, "carbon dioxide (e.g. under pressure) is added (preferably, continuously) to the polyurethane foaming composition (ie "white material") or to the polyisocyanate monomer and/or isocyanate-terminated prepolymer (ie "black material") or simultaneously to the polyurethane foaming composition and the polyisocyanate monomer and/or isocyanate-terminated prepolymers, before the two material streams (i.e. white material and black material) enter (e.g. continuously) to the mixer for mixing (or before the two material streams are transported into the mixer)" means that: at certain positions (for example, in respective delivery pipelines for the two material streams or in respective storage containers for the two material streams) after which the two material streams (i.e. white material and black material) enter (for example, continuously) into the mixer for mixing (or after which the two material streams are transported into the mixer), carbon dioxide (for example, under pressure) is added (discontinuously or continuously) into the polyurethane foaming composition (i.e. "white material") or to the polyisocyanate monomer and/or isocyanate-terminated prepolymer (ie "black material") or simultaneously to the polyurethane foaming composition and the polyisocyanate monomer and/or isocyanate-terminated prepolymer.

The organic amine (OA) is one or more selected from the group consisting of a primary amine compound (I), a secondary amine compound (II), a tertiary amine compound (III), a hydroxylamine, a polyalkylene polyamine, or a hydroxyl-substituted or $C_1$-$C_3$ alkyl-substituted polyalkylene polyamine:

In the above formula, $R^1$, $R^2$, $R^3$, $R^4$, $R^5$ and $R^6$ are each independently $C_1$-$C_8$ hydrocarbyl, $C_1$-$C_8$ hydroxyhydrocarbyl, $C_1$-$C_4$ hydroxyhydrocarbyloxy $C_1$-$C_4$ hydrocarbyl, $C_1$-$C_6$ aminohydrocarbyl, or $C_1$-$C_3$ alkylamino $C_1$-$C_4$ hydrocarbyl; preferably, $R^1$, $R^2$, $R^3$, $R^4$, $R^5$ and $R^6$ are each independently $C_1$-$C_4$ hydrocarbyl, $C_1$-$C_4$ hydroxyhydrocarbyl, $C_1$-$C_3$ hydroxyhydrocarbyloxy $C_1$-$C_3$ hydrocarbyl, $C_1$-$C_4$ aminohydrocarbyl or $C_1$-$C_2$ alkylamino $C_1$-$C_3$ hydrocarbyl; more preferably, $R^1$, $R^2$, $R^3$, $R^4$, $R^5$ and $R^6$ are each independently $C_1$-$C_2$ hydrocarbyl, $C_1$-$C_3$ hydroxyhydrocarbyl, $C_1$-$C_3$ hydroxyhydrocarbyloxy $C_1$-$C_3$ hydrocarbyl, $C_1$-$C_3$ aminohydrocarbyl or $C_1$-$C_2$ alkylamino $C_1$-$C_2$ hydrocarbyl.

In the present application, the hydrocarbyl group is preferably an alkyl group. The hydrocarbyloxy group is preferably an alkoxy group.

Preferably, the polymer polyol is selected from the group consisting of: polyether polyol, polyester polyol, polyether-polyester polyol, polycarbonate diol, polycarbonate-polyester polyol, polycarbonate-polyether polyol, polybutadiene polyol, or polysiloxane polyol; more preferably, the polymer polyol is a combined polyether polyol. The average functionality of polymer polyols (eg, combined polyether polyols) is generally 2-16, preferably 2.5-10, and more preferably 3-8.

Preferably, the above-mentioned polyalkylene polyamine is one or more selected from the group consisting of diethylenetriamine, triethylenetetramine, tetraethylenepentamine, dipropylenetriamine, tripropylenetetramine, or tetrapropylenepentamine.

Preferably, the foaming method described above is a supercritical carbon dioxide foaming method or a subcritical carbon dioxide foaming method using supercritical carbon dioxide or subcritical carbon dioxide.

Generally, the physical blowing agent is selected from at least one of the following: n-pentane, isopentane, cyclopentane, other alkanes having a boiling point in the range of 0-100° C., HCFC-141b, HFC-245fa, HFC-365mfc, LBA, hexafluorobutene, other chlorofluorocarbons having a boiling point in the range of 0-100° C., or methyl formate.

Generally, ammonia and/or hydrazine is added to the polyurethane foaming composition in the form of ammonia water or hydrazine hydrate, and the resulting polyurethane foaming composition contains 0.4-8 wt %, 0.5-7 wt %, preferably 0.6-6 wt. %, more preferably 0.7-5 wt % of water in total, the weight percentages are based on the total weight of the polyurethane foaming composition.

Preferably, the polyurethane foaming composition further comprises: a foam stabilizer, a polyurethane catalyst, and a flame retardant.

Preferably, the organic primary amine (I) is one or more selected from the group consisting of:

primary amine wherein $R^1$ is $C_1$-$C_8$ hydrocarbyl, such as methylamine, ethylamine, propylamine, butylamine, pentylamine, hexylamine, heptylamine, octylamine, nonylamine, decylamine, dodecylamine, tetradecylamine, cetylamine, octadecylamine, eicosylamine, tetracosylamine, unsubstituted or substituted (such as halogen substituted) aniline, unsubstituted or substituted (such as halogen substituted) benzylamine, cyclohexylamine, methylcyclohexylamine, cyclohexylmethylamine, N-methyl cyclohexylamine or N-methylbenzylamine and the like;

primary amine wherein $R^1$ is $C_1$-$C_8$ hydroxy hydrocarbyl, such as ethanolamine, propanolamine, butanolamine, chloroethanolamine, oxodiethylamine, and the like; and primary amine wherein $R^1$ is $C_1$-$C_6$ aminohydrocarbyl, such as ethylenediamine, propylenediamine, butylenediamine or pentamethylenediamine or hexamethylenediamine, and the like.

More preferably, the organic primary amine (I) is one or more selected from the group consisting of:

methylamine, ethylamine, propylamine, ethanolamine, propanolamine, oxodihexylamine, ethylenediamine, propylenediamine, etc.

Preferably, the organic secondary amine (II) is one or more selected from the group consisting of:

secondary amine wherein $R^2$ and $R^3$ are $C_1$-$C_8$ hydrocarbyl, that is, monoamines having a secondary amine group, such as dimethylamine, diethylamine, methylethylamine, dipropylamine, methylpropyl amine, ethylpropylamine, dibutylamine, ethylbutylamine, dipentylamine, dihexylamine, diheptylamine, dioctylamine, dinonylamine, didecylamine, di(dodecyl) amine, di(tetradecyl) amine, di(hexadecyl) amine, di(octadecyl) amine, di(icosyl) amine or di(tetradecosyl) amine and the like;

amine wherein $R^2$ and $R^3$ are $C_1$-$C_8$ hydroxyhydrocarbyl, such as diethanolamine, ethanolpropanolamine, dipropanolamine, hydroxyethylhydroxyisopropylamine, dihydroxyisopropylamine, or dihydroxychloropropyl amine and the like; and amine wherein $R^2$ is $C_1$-$C_8$ hydrocarbyl and $R^3$ is $C_1$-$C_8$ hydroxy hydrocarbyl, such as N-methyl ethanolamine, N-ethylethanolamine, N-isopropylhydroxyisopropylamine, or N-ethylhydroxyisopropylamine and the like.

More preferably, the organic secondary amine (II) is diethanolamine, ethanolpropanolamine, dipropanolamine or N-methylethanolamine.

Preferably, the tertiary amine compound (III) is one or more selected from the group consisting of:

amine (tertiary amine) wherein $R^4$, $R^5$, and $R^6$ are each independently $C_1$-$C_8$ hydrocarbyl (aliphatic group, cycloaliphatic group, aromatic group) or $C_1$-$C_8$ hydroxy hydrocarbyl or $C_1$-$C_6$ aminohydrocarbyl, such as triethylamine, N,N-dimethyl cyclohexylamine, N,N-dimethyl ethanolamine, N,N-dimethyl benzylamine, triethylenediamine, triethanolamine, N-ethyl diethanolamine, or tri(aminoethyl)amine, and so on.

More preferably, the tertiary amine compound (III) is triethanolamine.

In the foaming process, when carbon dioxide is mixed with a polyurethane foaming composition containing an organic amine (OA), the decomposition temperature of the amine carbonate salt formed by the carbon dioxide and the organic amine (OA) is generally between 50-70° C., preferably 55-65° C.

Preferably, the pH of the polyurethane foaming composition is 7.2-10, preferably 7.4-9.5, preferably 7.5-9, and more preferably 7.8-8.5.

The polyurethane foaming composition may further comprise: 0.1-5 wt %, preferably 0.3-4.5 wt %, more preferably 0.5-4 wt %, and more preferably 0.8-3 wt % (for example, 1.2 wt % or 1.8 wt % or 2.5 wt %) of organic amine (OA) carbonate, that is, the carbonate of the above-mentioned organic amine (OA). That is, a small amount of an organic amine (OA) carbonate is previously mixed into the polyurethane foaming composition. Preferably, the organic amine (OA) carbonate is an organic alkanolamine carbonate.

Preferably, in the polyurethane foaming method, a stream of a polyurethane foaming composition (ie, a foaming composition or a white material) and a stream of a polyisocyanate monomer and/or an isocyanate-terminated prepolymer (i.e. the isocyanate stream or black material) is mixed in a pressure mixer. Preferably, the pressure mixer is a foaming device having a pressure mixing zone or a mixer, such as a polyurethane high-pressure foaming machine or a polyurethane high-pressure spray-coating machine.

Preferably, the organic amine (OA) is an alkanolamine, preferably one or more selected from monoethanolamine, monopropanolamine, monoisopropanolamine, methyl amine, ethylamine or propylamine.

Preferably, the organic amine (OA) carbonate is one or more selected from the group consisting of (ammonium) (monoethanolamine) carbonate, di(ethanolamine) carbonate, (ethanolamine) (propanolamine) carbonate, di(propanolamine) carbonate, di (isopropanolamine) carbonate, di(methylamine) carbonate, di(ethylamine) carbonate, di(propylamine) carbonate, (methylamine) (ethylamine) carbonate, (methylamine) (propylamine) carbonate, (ethylamine) (propylamine) carbonate.

In the polyurethane foaming method, gaseous carbon dioxide, liquid carbon dioxide, subcritical carbon dioxide or supercritical carbon dioxide are stored in a pressure vessel, respectively. Prior to mixing and foaming, gaseous carbon dioxide, liquid carbon dioxide, subcritical carbon dioxide and/or supercritical carbon dioxide are fed as a stream into the polyurethane foaming composition (i.e, foaming composition or white material), or into a polyisocyanate monomer and/or an isocyanate-terminated prepolymer (i.e., an isocyanate stream or black material), or both into a white material and a black material, and the two streams are then fed into a pressure mixer for mixing. The stream of white material and the stream of black material (preferably under pressure) are mixed and discharged for foaming, thereby preparing a polyurethane foam material. The polyurethane foaming method of the present invention is particularly suitable for spray foaming or cast foaming.

Generally, the polyurethane foaming composition (white material) and the polyisocyanate monomer and/or isocyanate-terminated prepolymer (black material) are stored in separate containers (preferably pressure vessels) before being conveyed into the pressure mixer; and the polyurethane foaming composition has been mixed uniformly before being transferred into the pressure mixer so that organic amines (OA), preferably alkanolamine, are uniformly mixed in the polyurethane foaming composition.

In the present application, the polyisocyanate monomer and/or isocyanate-terminated prepolymer refer to: a polyisocyanate monomer, an isocyanate-terminated prepolymer, or a mixture or combination of both a polyisocyanate monomer and an isocyanate-terminated prepolymer.

Preferably, the organic amine (OA) is an alkanolamines, preferably one or more selected from monoethanolamine, monopropanolamine, monoisopropanolamine, methyl amine, ethylamine or propylamine.

Preferably, the organic amine (OA) carbonate is one or more selected from the group consisting of (ammonium) (monoethanolamine) carbonate, di(ethanolamine) carbonate, (ethanolamine) (propanolamine) carbonate, di(propanolamine) carbonate, di(isopropanolamine) carbonate, di(methylamine) carbonate, di(ethylamine) carbonate, di(propylamine) carbonate, (methylamine) (ethylamine) carbonate, (methylamine) (propylamine) carbonate, and (ethylamine) (propylamine) carbonate.

In the present application, gaseous carbon dioxide, liquid carbon dioxide, subcritical carbon dioxide or supercritical carbon dioxide, referred to as carbon dioxide briefly, is called a blowing agent or a primary blowing agent (for example, when other physical blowing agents are included), thus the organic amine is called an auxiliary foaming agent.

In the present application, for the definition of subcritical (state) carbon dioxide and supercritical (state) carbon dioxide, refer to JP2011213854A, JP2009256484A, JP2002047325A, JP2002327439A, JP2016188329A, and JP2016188330A. The subcritical state carbon dioxide refers to carbon dioxide in a liquid state in which the pressure is equal to or higher than the critical pressure of carbon dioxide and the temperature is lower than the critical temperature. The supercritical (state) carbon dioxide refers to carbon dioxide in which the pressure is not lower than the critical pressure of carbon dioxide and the temperature is not lower than the critical temperature. These Japanese patents are incorporated herein by reference in their entirety.

In addition, according to a sixth embodiment of the present invention, a method for preparing an alkanolamine carbonate is provided.

The inventors of the present application unexpectedly found that a part of or all of aqueous alkanolamine carbonate mixture in a liquid state obtained by reacting an ammonium carbonate or hydrazine carbonate with an epoxide in the presence of water as a solvent or dispersing medium can be further used as a solvent or a dispersing medium in the reaction of ammonium carbonate or hydrazine carbonate with an epoxide to prepare a liquid-state alkanolamine carbonate mixture with lower water content. As such, an alkanolamine carbonate mixture with low water content (e.g. 5-10 wt %) can be prepared finally.

According to the present invention, a method for preparing an alkanolamine carbonate is provided, the method comprises:

(1) a first raw material and a second raw material are reacted in the presence of water, optionally in the presence of a catalyst, to obtain a liquid-state alkanolamine salt mixture (MAA1) with a water content (W1) of less than 60 wt % (for example, 20-60 wt %, such as 25-40 wt %); and (2) a part or all of the liquid alkanolamine salt mixture (MAA1) obtained in step (1) is used as a dispersion medium or as a solvent, add the first raw material and the second raw material are added thereto and mixed; then, optionally in the presence of a catalyst, the resultant reaction mixture is reacted to obtain an alkanollamine salt mixture (MAA2) in liquid state wherein its water content (W2) is further reduced to be lower than the water content (W1) of the product obtained in step (1) (for example, its water content W2 is less than 50 wt %, e.g. 10-50 wt %, such as 15-30 wt %);

wherein the first material is one or more selected from a group consisting of following compounds:

$H_2N-COONH_4$, $(NH_4)_2CO_3$, hydrazinium carbonate, ammonium hydrazinium carbonate, or organic amine compound (M) carbonate;

$HCOONH_4$, hydrazinium formate, or organic amine compound (M) formate, $HO-COONH_4$, hydrazinium bicarbonate, or bicarbonate of organic amine compound (M);

the second material is one or more selected from following epoxides:

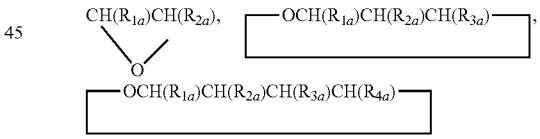

or styrene oxide; wherein $R_{1a}$, $R_{2a}$, $R_{3a}$ or $R_{4a}$ each independently is selected from the following groups: H, $C_1$-$C_7$ aliphatic hydrocarbyl group optionally substituted by hydroxyl or amino or halogen, $C_3$-$C_7$ cycloaliphatic hydrocarbyl group optionally substituted by hydroxyl or amino or halogen, or, $C_6$-$C_{10}$ aromatic hydrocarbyl group optionally substituted by hydroxyl or amino or halogen;

wherein the organic amine compound (M) is an organic amine compound selected from following compounds:

$C_1$-$C_{24}$ hydrocarbyl amines;

Di-($C_1$-$C_{16}$ hydrocarbyl) amines;

$C_2$-$C_{14}$ hydrocarbylene diamines;

$C_4$-$C_{16}$ polyalkylene polyamines;

$C_3$-$C_{18}$ organic triamines having three primary amine groups or $C_5$-$C_{18}$ organic tetramines having four primary amine groups; or $C_2$-$C_{10}$ alkanolamines.

Preferably, the amount of water used in step (1) is 60-250 wt %, preferably 80-200 wt %, more preferably 100-170 wt %, and more preferably 110-160 wt % based on the weight of the first raw material.

Preferably, the method further comprises:

(3) a part or all of the liquid alkanolamine salt mixture (MAA2) obtained in step (2) is used as a dispersion medium or as a solvent, and the above-mentioned first raw material and the above-mentioned second raw material are mixed therein; then, optionally in the presence of a catalyst, the resultant reaction mixture is allowed to react to obtain an alkanolamine salt mixture (MAA3) in liquid state wherein its water content (W3) is further reduced to be lower than that of the product (MAA2) obtained in step (2) (for example, its water content W3 is lower than 40 wt %, such as 6-40 wt %, such as 7-20 wt %).

Preferably, the method further comprises:

(4) a part or all of the liquid alkanolamine salt mixture (MAA3) obtained in step (3) is used as a dispersion medium or as a solvent, and the above-mentioned first raw material and the above-mentioned second raw material are mixed therein; then, optionally in the presence of a catalyst, the resultant reaction mixture is allowed to react to obtain an alkanolamine salt mixture (MAA4) in liquid state wherein its water content (W4) is further reduced to be lower than that of the product (MAA3) obtained in step (3) (for example, its water content W4 is lower than 30 wt %, such as 2-30 wt %, more preferably 3-25 wt %, more preferably 3.5-20 wt wt %, such as 7 wt % or 12 wt %).

In the above-described method, it is preferred that:

$R_{1a}$, $R_{2a}$, $R_{3a}$ or $R_{4a}$ each independently is selected from the following groups: H, methyl, or ethyl optionally substituted by hydroxyl or amino or halogen, propyl or isopropyl optionally substituted by hydroxyl or amino or halogen, cyclohexyl optionally substituted by hydroxyl or amino or halogen, or, phenyl or methylphenyl optionally substituted by hydroxyl or amino or halogen; preferably, $R_{1a}$, $R_{2a}$, $R_{3a}$ or $R_{4a}$ each independently is selected from the following groups: H, methyl, chloromethyl, bromomethyl, ethyl, cyclohexyl, or phenyl.

In the above method, it is preferable that:

The water content (W2) of the alkanolamine salt mixture (MAA2) obtained in step (2) is 30-85% (preferably 35-80%, more preferably 40-75%, such as 50% or 60%) of the water content (W1) of the alkanolamine salt mixture (MAA1) obtained in step (1).

Further preferably, the water content (W3) of the alkanolamine salt mixture (MAA3) obtained in step (3) is 30-85% (preferably 35-80%, more preferably 40-75%, such as 50% or 60%) of the water content (W2) of the alkanolamine salt mixture (MAA2) obtained in step (2).

Further preferably, the water content (W4) of the alkanolamine salt mixture (MAA4) obtained in step (4) is 30-80% (preferably 35-75%, more preferably 40-70%, such as 50% or 60%) of the water content (W3) of the alkanolamine salt mixture (MAA3) obtained in step (3).

In the above method, preferably, the epoxide is: ethylene oxide, propylene oxide, epichlorohydrin, bromopropylene oxide (epibromohydrin), butylene oxide, or epoxy chlorobutane or styrene oxide, or a mixture of any two or more of them.

In the above method, preferably, the catalyst is aqueous ammonia.

In the above method, for steps (1) and (2), or for steps (1), (2), and (3), or for steps (1), (2), (3), and (4), these steps can be independently performed in the same or different places or in the same or different workshops. For example, step (1) is performed in one city, and step (2) is performed in another city.

According to the present invention, there is also provided a blowing agent mixture comprising the above-mentioned alkanolamine salt mixture and a physical blowing agent. The alkanolamine salt mixture is one or more selected from the alkanolamine salt mixture (MAA1), (MAA2), (MAA3), or (MAA4); preferably, the alkanolamine salt mixture is one or more selected from alkanolamine salt mixtures (MAA2), (MAA3) or (MAA4). The physical blowing agent is at least one selected from the following group: n-pentane, isopentane, cyclopentane, or other alkanes having a boiling point in the range of 0-100° C., HCFC-141b, HFC-245fa, HFC-365mfc, LBA, FEA-1100 (hexafluorobutene), or other chlorofluorocarbons having a boiling point in the range of 0-100° C., or methyl formate.

For the content that is not described in detail in this application, reference can be made to CN107089927A or CN107089910A, and the content of their specification is incorporated into this application for reference.

Beneficial Technological Effects or Advantages of Present Invention

A) In the first to fourth embodiments of the invention:

1. By combining the alkanolamine salt mixture (MAA) with hexafluorobutene as a polyurethane foaming agent, the prepared polyurethane foam material not only has better thermal insulation properties at normal temperature, but also has good resistance to deformation and good thermal insulation properties at low or ultra low temperature. Their application in the field of cryogenics has significant advantages.

2. By using the alkanolamine salt mixture (MAA) and hexafluorobutene in combination as a polyurethane foaming agent, during the foaming process, the first foaming stage is performed by hexafluorobutene, and the second foaming stage is performed by decomposing of the compounds of general formula (I) in the alkanolamine salt mixture (MAA) to releases carbon dioxide for secondary foaming. As the foaming process presents a "double-peak" type, the two gases strongly support the cells and avoid cell collapsing, and make the cell size in the foam material relatively uniform. And still, through the cross-linking and chain extension of the decomposition product (alkanolamine) of the compound of general formula (I), the microstructure in the foam is strengthened, and the deformation resistance of the foam is very outstanding.

3. The dimensional change rate or shrinkage rate of the polyurethane foam material prepared by using the composite foaming agent of the present invention as a foaming agent is ≤0.3%, or even ≤0.2% (according to Chinese National Standard GB/T 8811-2008, the storage time of the foam can be as required in the standard). In addition, for example, at a foam density of 34-42 Kg/m3, the thermal conductivity w/m·k (10° C.) or w/m·k (22.5° C.) is between 0.01830-0.01895, preferably between 0.01850-0.01885. The thermal conductivity of the polyurethane foam in the prior art at this density is generally higher than 0.01900, and more usually higher than 0.02200. In addition, within this density range, the compressive strength of the foam of the present invention is in the range of 110-220 KPa, preferably in the range of 150-200 KPa.

B) In a fifth embodiment of the invention:

1. By uniformly mixing the organic amine (OA) in the foaming composition (white material) in advance, when using carbon dioxide for foaming, it is not necessary to use a stirring device for uniform mixing for a long time under high pressure. When the white material and the black material are charged into the pressure mixer under higher pressure and mixed, the carbon dioxide can be quickly and uniformly mixed and dispersed in the white material (for example, the mixing time in spray foaming is 0.1-10 seconds, such as 0.2-2 seconds). Moreover, more carbon dioxide can be absorbed in the white material, and thus a polyurethane foam material having uniformly distributed cells is obtained. Further, the size of the cells is very uniform, and the average size of the cells in the foam is larger than that of the foam material obtained by using ordinary supercritical foaming technology, the cell size of the former is almost 1.5-4 times that of the latter. In particular, by adding a small amount of an organic amine carbonate, especially an alkanolamine carbonate, to the white material, the above advantages become more prominent and obvious. Particularly, when alkanolamine is preliminarily mixed in white materials or when a small amount of an organic alkanolamine (OA) carbonate is uniformly mixed in advance in a foaming composition (white materials) in advance, the obtained foam material under cryogenic conditions (e.g. −160° C.) has excellent deformation resistance and excellent thermal insulation properties. Because carbon dioxide is fully absorbed by the white material, the pressure during the foaming operation is greatly reduced.

2. The foaming composition comprising an organic amine (OA) (for example, an organic amine compound of the general formula (I), (II), or (III)) of the present invention is stable at room temperature on the one hand, and on the other hand, in the course of polyurethane foaming, carbon dioxide gas can be released at a reasonable rate when the foaming reaction system is heated, so that the resultant foam material has ideal properties, such as the distribution density of the cells and the uniformity of the cell size.

3. The amine carbonate formed by carbon dioxide and organic amine can be uniformly dissolved or distributed at the molecular level in polymer polyols such as polyether polyols and/or polyester polyols to ensure uniform foaming and avoid local excessive foaming.

4. For the amine carbonate formed by carbon dioxide and organic amines, certain decomposition products, i.e., primary and/or secondary amine compounds, produced after $CO_2$ is released due to the decomposition of the amine carbonate in the liquid $CO_2$ foaming process, still contain at least one active hydrogen, which are suitable as a chain extender and/or cross-linking agent. The compound of the general formula (I), (II) or (III) of the present invention serves as both a "foaming point" and a "chain extension point" and/or a "crosslinking point", which significantly enhances the mechanical strength of the cells. The obtained polyurethane foam has good dimensional stability. After the finished polyurethane foam is left for several months or even one year, its shrinkage is hardly observed with the naked eye, and there is no collapse phenomenon of foam. In particular, it has good dimensional stability after being left at a higher temperature (such as 40-70° C.) for a long time, such as 10 days.

5. For the organic amine (for example, an organic amine compound of the general formula (I), (II) or (III)) of the present invention, especially when a part of the tertiary amine compound is included therein, amine carbonate (especially tertiary amine carbonate) formed from carbon dioxide and an organic amine (particularly a tertiary amine compound) can release $CO_2$ after decomposition, and the decomposition product produced is suitable as a catalyst to promote the polyurethane foaming process.

6. The organic amine of the present invention is not easily volatile, does not contain metal ions (metal ions are corrosive to metal substrates), and the amine carbonate formed from it can completely or mostly replace chlorofluorocarbon blowing agents. It has important significance in terms of environmental protection, and the foaming effect is obviously better than that of other foaming agents used in the prior art.

7. When a carbonate of an organic amine (OA) (for example, an organic amine compound of the general formula (I), (II), or (III)) is mixed with a chlorofluorocarbon such as HCFC-141b, or HFC-365mfc to be used as a blowing agent, it can significantly improve the thermal insulation performance of foam materials, compared with the use of chlorofluorocarbon blowing agent alone. At present, it is common to select a specific polyether polyol that has good compatibility or miscibility with the relevant blowing agent according to the blowing agent or a specific chlorofluorocarbon blowing agent, but when using the blowing agent of the present invention. It does not require to select specific polyether polyols or polyester polyols, so the blowing agent has a wide range of applications. Various types of polyester polyols and/or polyether polyols can be used in the foaming composition. On the other hand, if the additives such as polyethers that are suitable for the polyurethane foaming agent prepared by the present invention are selected, better performance will be obtained.

8. The dimensional change rate or shrinkage rate of the polyurethane foam material prepared by using organic amines (such as organic amine compounds of general formula (I), (II) or (III)) as $CO_2$ solubilizers is ≤5%, preferably ≤3%, more preferably ≤1%, more preferably ≤0.5% (according to Chinese National Standard GB/T 8811-2008, but the storage time is 5 months).

C) In a sixth embodiment of the invention:

The invention can prepare an alkanolamine salt compound with low water content, and when the latter is used to prepare a polyurethane foam material, the adverse effect of water on the foaming reaction is avoided. It is also suitable for use as a blowing agent in combination with a physical blowing agent. The physical blowing agent is selected from at least one of the following groups: n-pentane, isopentane, cyclopentane, or other alkanes having a boiling point in the range of 0-100° C., HCFC-141b, HFC-245fa, HFC-365mfc, LBA, FEA-1100 (hexafluorobutene), or other chlorofluorocarbons with a boiling point in the range of 0-100° C., or methyl formate.

DETAILED DESCRIPTION OF THE INVENTION

Figure 1:
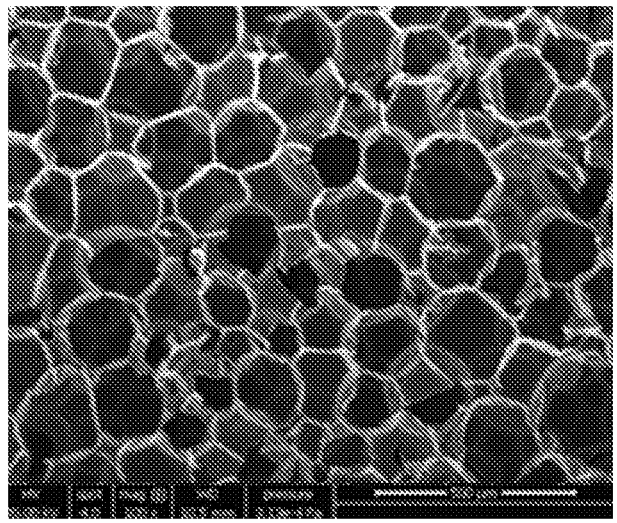
FIG. 1 is a scanning electron microscope (SEM) photograph of the foam of example 2.

The further description for present invention is made by reference to the following examples.

In the present application, the polyether polyols or the polyester polyols usually used to prepare polyurethane foam or used in foaming composition are selected from following: polyether 4110, 450, 400A, MN500, SU380, SA380, 403, SA460, or G350; polyester CF6320, DM2003, YD6004, AKS7004, or CF6255. The frequently used catalyst is selected from: 33LV(A-33): 33% dipropylene glycol solution of triethylenediamine, N,N-dimethylethanolamine, N,N-dimethyl benzylamine, 70% dipropylene glycol solution of di(dimethylaminoethyl)ether, 70% diethylene glycol solution of potassium octanoate, dibutyltin dilaurate, PT303, PT304, postassium acetate, PC-8(N,N-dimethyl cyclohexylamine), PC-5, PC-41, triethanolamine, JXP-508, JXP-509, TMR-2, TMR-3, or TMR-4. The usually used flame retardants: TCPP, TCEP, DMMP, ammonium chloride, aluminium hydroxide powder, DM1201, DM1301, tetrabromophthalate diol. The usually used silane surfactants: DC8545, AK-158, AK-8805, AK-8812, AK-8809, AK-8818, AK-8860, DCI990, DC5188, DC6070, DC3042, or DC3201. Non-silane surfactants: LK-221, or LK-443.

The safety instructions: for safety in case of using epoxide compound in the present invention, the reactor must be treated and protected with inert gases (such as nitrogen gas or argon gas) before and after the reactants are charged into the reactor in order to avoid explosion. Additionally, for safety in case of adding ethylene oxide, it is preferred that ethylene oxide is added batchwise to the reactor, whereas propylene oxide can be added to reactor all at once or also batchwise. The reactor is generally a pressure reactor equipped with a cooling device, unless otherwise stated. The epoxide compound should be slowly added to the reactor in batches, whereas even those relatively safe epoxides should also be slowly added to the reactor in batches, as well as should control the reaction conditions such as reaction rate to ensure safety. The hydrazine hydrate is also a flammable, explosive and toxic compound, therefore, it must also be used in accordance with the relevant requirements and regulations.

The various properties of foam are tested according to Chinese National Standards GB/T 26689-2011 (the rigid polyurethane foamed plastics for refrigerators and refrigerating cabinets) in following examples. The dimension of testing specimen is generally 10*10*2.5 cm.

The coefficient of heat conductivity is tested according to Chinese National Standards GB/T 10294-2008 or GB/T 10295-2008. The average temperature used is 10° C., and cold-hot-plate temperature difference is 15-20° C. The apparent (core) density of the foam is tested according to GB/T 6343-2009. The low temperature dimensional stability of the foam is tested according to GB/T 8811-2008 under the temperature of −30° C.±2° C. The compression strength of the foam is tested according to GB/T 8813-2008. The closed-cell ratio (i.e., closed-cell volume percentage) of the foam is tested according to GB/T 10799-2008.

With respect to the measuring method of the content of various alkanolamines (such as monoethanolamine, diethanolamine, triethanolamine, monopropanolamine, dipropanolamine or tripropanolamine) in the compounds of the general formula (I) or the compound mixture comprising such compounds, the gas chromatography can be used. The gas chromatograph is fitted with hydrogen flame ionization detector (FID), and the mass concentration of the compound of the general formula (I) is about 10 mg/mL, used as a standard solution. The gas phase chromatography conditions: HP-5 adsorption capillary column (30 m*0.32 mm i.d.*0.25 μm, 5% phenyl methyl-siloxane); the column temperature is regulated by temperature programming, its initial temperature is set at 80° C. and maintained for 3 min., then the column temperature is increased to 250° C. at the heating rate of 25° C./min and maintained for 5 min.; wherein the injection port temperature is 250° C.; the detector temperature is 260° C.; the carrier gas is high purity nitrogen gas, and its flow rate is 1.5 mL/min.; the combustible gas is hydrogen gas, and its flow rate is 30 mL/min.; the combustion-supporting gas is air, and its flow rate is 300 mL/min.; the makeup gas is nitrogen gas, and its flow rate is 25 mL/min.; the manner of sample injection is split stream sampling, the split ratio: 30:1, and the sample size for it is 1 μL.

Part I: First to Fourth Embodiments According to the Invention

A) To Prepare the Compound of the General Formula (I) from Ammonium Carbamate

Example A-1

1.4 tons or ammonium carbamate (molecular weight 78.07), and 1.2 ton of water are charged into a stainless steel autoclave equipped with cooling water jacket (hereinafter referred to reactor, for short), start the stirrer to make ammonium carbamate dissolve, purge the reactor with nitrogen gas, then close the reactor and start the stirrer again; 1.90 tons of propylene oxide (molecular weight 58.08, boiling point 34° C.) is feed into the reactor, wherein the charging rate of propylene oxide should be controlled so as to keep the pressure in the reactor to a pressure not more than 0.6 MPa, heat up the reaction system slowly with continual agitation, and let the reaction system to react for 15 hours with the reaction temperature being controlled to less than 70° C.; after the completion of the reaction, the temperature of the reaction system is lowered slowly to 50° C., and then, some unnecessary water (e.g. to water content of less than 20 wt %) and the unreacted propylene oxide are removed slowly from the reaction system with the vacuum level controlled to below 600 mmHg (preferably below 500 mmHg); then the vacuum therein is released and after the temperature of the reaction system is lowered slowly to below 40° C., the reaction product is discharged to obtain compound A-1 (i.e, alkanolamine salt mixture MAA). The viscosity of the reactant is 200 Centipoise, and its pH=9.

The decomposition temperature of the compound A-1 is in a range of 45-70° C. (it begins to slowly decompose at 45° C., and its peak decomposition temperature is 57-62° C.). The content of alkali metal ion and alkaline earth metal ion of the compound A-1 is determined by the atomic absorption spectrophotometer (Seiko Instruments, Inc.; SAS/727) to be below the detection limit. By the gas chromatographic analysis, the mole ratio of monopropanol amine to dipropanol amine is 1:0.18. The compound A-1 contains about 74 wt % of both salts of the monopropanol amine and dipropanol amine. It still contains a part of water. Additionally, the compound A-1 contains about 55 wt % of monopropanol amine and dipropanol amine (analyses on residues obtained after heating the compound A-1 to release carbon dioxide), based on total weight of the compound A-1 before thermal decomposition.

The compound A-1 is a transparent or clear liquid which is relatively stable at ambient temperature or under environmental condition and is suitable for using as polyurethane foaming agent, and its basic characteristics, compared to HFC-245fa, LBA or pentafluorobutane, are as follows:

| | Compound A-1 | HFC245fa | Pentafluorobutane | LBA |
|---|---|---|---|---|
| ODP | 0 | 0 | 0 | 0 |
| GWP | 1 | 1030.01 | 793.98 | 5.00 |
| Boiling Point (° C.) | Begin to decompose slowly at 45° C. | 15.3 | 40.2 | 19.3 |

It is observed from above table that, compound A-1 has the GWP (greenhouse warming potential value) of 1, relatively high decomposition temperature, it can overcome many shortcomings of some physical foaming agents with low boiling point (below 20° C.) such as HFC-245fa, LBA or pentafluorobutane, for instance their GWP of far larger than 1, relatively low boiling points and volatile properties, whereas the compound A-1 of the present invention has the GWP of 1, much higher boiling point, and ODP (ozone depletion potential value) of 0, and is not easy to volatilize, so it does not destroy the atmospheric ozone layer. Further, the transportation and storage of the compound A-1 is convenient due to its lower volatility.

Example A-2

1 kg of ammonium carbamate and 1.1 kg of water are charged to a transparent quartz glass reactor and stirred to dissolve ammonium carbamate, and the reactor is purged with nitrogen gas, thereto 2.1 kg of propylene oxide is added and stirred, the resultant reaction system is heated up slowly with continual agitation, and reacted at the temperature controlled to 50-60° C. and the pressure of no more than 0.6 MPa. When the reaction is conducted for about 2 hours, a fantastic phenomen bursts into view: the turbid and opaque mixture instantly become to a transparent or clear solution. The reaction continues for 8 hours; then the temperature of the reaction system is reduced to 50° C., and also the unnecessary water and the unreacted propylene oxide are removed from the reaction system under a vacuum level of 600 mHg; after the temperature of the mixture is cooled to below 40° C., the resulting product is discharged. The reaction time is sufficient to make the reaction be finished according to the mole ratio of the reactants. Compound A-2 is obtained with the viscosity of 200 centipoise, pH=9.1, and the decomposition temperature in a range of 45-70° C. It is indicated from the liquid chromatography analysis and the gas chromatographic analysis that compound A-2 is a mixture comprises more than one of alkanolamines. Its water content is 20.5 wt %.

Example A-3

7 kg of ammonium carbonate, 7 kg of ammonium carbamate and 15 kg of water are charged to a reactor and stirred to dissolve ammonium carbonate and ammonium carbamate. The reactor is purged with nitrogen gas and thereto 32 kg of propylene oxide is added batchwise; the resultant reaction system is heated up slowly with continual agitation, and the reaction is conducted for 10 hours at the temperature controlled to 45-70° C. and the pressure controlled to no more than 0.6 MPa. The temperature of the reaction system is reduced to 50° C., and also the unnecessary water and unreacted propylene oxide are removed from the reaction system under a vacuum level of 600 mmHg and a temperature below 50° C.; after the temperature of the reaction system is cooled to below 40° C., the vacuum is released, the resulting product is discharged, so as to obtain compound A-3. Its viscosity is about 250 centipoise, pH=9, and its decomposition temperature is in a range of 45-70° C.

Example A-4

16 kg of monoethanolamine carbamate and 18 kg of water are charged to a reactor, the reactor is purged with nitrogen gas and stirred to dissolve the monoethanolamine carbamate, and thereto 13 kg of propylene oxide is added batchwise; agitation is started, the pressure is controlled to no more than 0.6 MPa, the resultant reaction system is heated up slowly with continual agitation; when the temperature of the reaction system is increased to 70° C., the system is reacted for 5 hours at this temperature; then the temperature of the reaction system is reduced to below 50° C., and also the unnecessary water and unreacted propylene oxide are removed from the reaction system under a vacuum level of 600 mmHg; finally, after the temperature of the reaction system is cooled to below 40° C., the vacuum is released, the resulting product is discharged, so as to obtain compound A-4. The viscosity of the reaction mixture is 280 Centipoise, and its pH=9. The decomposition temperature of the compound is in a range of 45-70° C.

Example A-5

21 kg of diethylene triamine carbamate and 15 kg of water are charged to a reactor and stirred to dissolve the diethylene triamine carbamate, the reactor is purged with nitrogen gas, and thereto 16 kg of propylene oxide is added batchwise with agitation at the pressure controlled to no more than 0.6 MPa and the temperature of 45-70° C. After the addition of propylene oxide is finished, the reaction is carried out for 5 hours at this temperature; and then the temperature of the reaction system is reduced to 50° C., and also the unnecessary water and unreacted propylene oxide are removed from the reaction system under a vacuum level of 600 mmHg; and, after the temperature of the reaction system is cooled to below 40° C., the vacuum is released, the resulting product is discharged, so as to obtain compound A-5. Its viscosity is about 350 centipoise, pH=9, and its decomposition temperature is in a range of 45-70° C.

Example A-6

1.2 kg of ammonium carbonate, 1.2 kg of ammonium carbamate and 2.7 kg of water are charged to a reactor and stirred to dissolve ammonium carbonate and ammonium carbamate, the reactor is purged with nitrogen gas, and thereto 7.1 kg of styrene oxide (molecular weight 120.15) is added; the resultant reaction system is heated up slowly with continual agitation, and the reaction is carried out for 10 hours at the temperature controlled to a range of 45-70° C. and the pressure controlled to no more than 0.6 MPa; then the temperature of the reaction system is reduced to 50° C., and also the unnecessary water is removed from the reaction system under a vacuum level of 600 mmHg and at a temperature below 50° C.; After the temperature of the reaction system is cooled to below 40° C., the vacuum is released, the resulting product is discharged, so as to obtain compound A-6. Its viscosity is about 460 centipoise, pH=9, and its decomposition temperature is in a range of 45-70° C.

B) To Prepare the Compounds of the General Formula (I) from Ammonium Carbonate or Hydrazinium Carbonate Example B-1

16 kg of ammonium carbonate (molecular weight 96), and 15.5 kg of water are charged to a reactor and stirred to dissolve ammonium carbonate, the reactor is purged with nitrogen gas, thereto 28 kg of propylene oxide is added and stirred, and under the pressure controlled to no more than 0.6 MPa, the resultant reaction system is heated up slowly with continual agitation. The reaction is carried out for 12 hours while its temperature is controlled to below 70° C. After the reaction is finished, the temperature of the reaction system is reduced to 50° C. slowly, and also the unnecessary water and unreacted propylene oxide are removed from the reaction system under a vacuum level of 600 mmHg. The temperature of the reaction system is cooled to below 40° C., the vacuum is released, the resulting product is discharged, so as to obtain compound B-1. Its viscosity is about 300 centipoise, pH=8.9, and the decomposition temperature of the compound B-1 is in a range of 45-70° C. It is indicated from the liquid chromatography analysis and the gas chromatographic analysis that compound B-1 is a mixture comprises more than one of alkanolamines.

The content of alkali metal ion and alkaline earth metal ion of the compound A-1 is determined by the atomic absorption spectrophotometer (Seiko Instruments, Inc.; SAS/727) to be below the detection limit. By the gas chromatographic analysis, the mole ratio of monopropanol amine to dipropanol amine is 1:0.28. The compound B-1 contains about 79 wt % of both salts of the monopropanol amine and dipropanol amine. The compound B-1 contains about 59 wt % of monopropanol amine and dipropanol amine (analyses on residues obtained after heating the compound B-1 to release carbon dioxide), based on total weight of the compound B-1 before thermal decomposition.

Example B-2

0.95 kg of hydrazinium carbonate (as 50 wt % hydrazinium carbonate aqueous solution, the volume of the aqueous solution is 1.8 L) and 0.8 kg of water are charged to a transparent quartz glass reactor and stirred, the reactor is purged with nitrogen gas, and thereto 1.8 kg of propylene oxide is added batchwise and stirred, the resultant reaction system is heated up slowly with constant stirring, and the reaction is conducted at the temperature controlled to a range of 50-70° C. and the pressure controlled to no more than 0.6 MPa. When the reaction goes on for about 2 hours, a fantastic phenomen bursts into view: the turbid and opaque mixture instantly become to a transparent or clear solution; the reaction continues for 5 hours, and then the temperature of the reaction system is reduced to 50° C., and also a part of water and the unreacted propylene oxide are removed from the reaction mixture under a vacuum level of 600 mmHg. After the temperature of the mixture is cooled to below 40° C., the resulting product is discharged. The reaction time is sufficient to make the reaction be finished according to the mole ratio of the reactants, so as to obtain compound B-2. Its pH=9.1, and its decomposition temperature is in a range of 45-70° C.

Example B-3

10 kg of ammonium carbonate and 11 kg of water are charged to a transparent quartz glass reactor and stirred to dissolve ammonium carbonate, the reactor is purged with nitrogen gas, and thereto 22 kg of propylene oxide is added with continual agitation while the temperature of the reaction system is controlled to a range of 45-70° C. and the pressure is controlled to no more than 0.6 MPa, and the reaction is continued. After the reaction goes on for about 2 hours, a fantastic phenomen bursts into view: the turbid and opaque mixture instantly becomes to a transparent or clear solution; the reaction is allowed to continue for 8 hours; thereafter the temperature of the reaction system is reduced to 50° C., and also the unnecessary water and the unreacted propylene oxide are removed from the reaction system under a vacuum level of 600 mmHg. The temperature of the mixture is cooled to below 40° C., the vacuum is released, and the resulting product is discharged, so as to obtain compound B-3. Its viscosity is about 340 centipoise, pH=9.1, and its decomposition temperature is in a range of 45-70° C.

C) To Prepare the Compounds of the General Formula (I) Containing Formate (HCOO⁻)

Example C-1

15 kg of ammonium formate, 1 kg of methylamine catalyst, 10 kg of water and 5 kg of ethylene glycol are added to a reactor and stirred, the reactor is purged with nitrogen gas, and thereto 12 kg of ethylene oxide is added batchwise at the pressure controlled to no more than 0.5 MPa and the temperature of no more than 120° C. and the reaction is conducted for 5 hours. After the reaction is finished the temperature of the reaction mixture is lowered; the unnecessary water and unreacted ethylene oxide are removed from the mixture under a reduced pressure where the vacuum level therein is controlled to below 600 mmHg and the temperature controlled to below 100° C. The vacuum is released, and the temperature of the reaction mixture is lowered to less than 50° C.; and the resulting product is discharged, so as to obtain compound C-1. Its viscosity is about 200 centipoise, pH=8.5, and its decomposition temperature is higher than 100° C.

Example C-2

The example C-1 is repeated except that 15 kg of propylene oxide is used to substitute 12 kg of ethylene oxide, and also propylene oxide is added into the reactor in a manner of one shot but not in a manner of batchwise. Compound C-2 is obtained. Its viscosity is about 350 centipoise, pH=8.6, and its decomposition temperature is higher than 100° C.

D) To Prepare the Compounds of the General Formula (I) Containing Bicarbonate Radical (HO—COO—)

Example D-1

10 kg of ammonium bicarbonate (molecular weight 79.06), 9.0 kg of water and 1 kg ethylene diamine are charged to a transparent quartz glass reactor and stirred to dissolve ammonium bicarbonate (allowing some insoluble ammonium bicarbonate to exist), the reactor is purged with nitrogen gas and then sealed. 20 kg of propylene oxide is added batchwise to the reactor with continual agitation while the temperature of the reaction system is controlled to a range of 45-65° C. and its pressure is controlled to no more than 0.6 MPa. The reaction is carried out for 10 hours at the controlled temperature The temperature of the reaction system is reduced to 50° C., and also the unnecessary water and unreacted propylene oxide are removed from the reaction mixture under a vacuum level below 600 mHg. After the temperature of the reaction system is cooled to below 40° C., the vacuum is released, and the resulting product is discharged, so as to obtain compound D-1. Its viscosity is about 250 centipoise, pH=8, and its decomposition temperature is in a range of 36-42° C.

The inventors discover surprisingly that the decomposition temperature of the compound D-1 dissolved in the white material can be increased to 45-65° C. when the compound D-1 is mixed with polyether polyol and/or polyester polyol, for example to formulate a foaming composition ("white material"). This make the compound D-1 have appropriate decomposition temperature, and hence, are suitable to be used in polyurethane foaming.

APPLICATION EXAMPLES

Example 1

5 parts by weight of the compound A-1 as foaming agent prepared by above example A-1, 4 parts by weight of hexafluorobutene (Dupont, trade name FEA-1100), 50 parts by weight of polyether polyol 4110 (BEFAR GROUP CO., LTD., BingZhou, Shandong, China), 1 part by weight of foam stabilizer DC3201 (Air Products and Chemicals, Inc., America), 12.5 parts by weight of flame retardant TCPP (Jiangsu Yoke Chemical Co., Ltd., China), and 2 parts by weight of catalyst A33 (33LV, Air Products and Chemicals, Inc., America) are mixed to obtain a transparent foaming composition, and then 95.5 parts by weight of isocyanate MDI (PM200, WANHUA CHEMICAL GROUP CO., LTD.)

is added to the composition, to obtain a polyurethane foam material by stirring and foaming.

Example 2

3 parts by weight of the compound B-1 as foaming agent prepared by above example B-1, 6 parts by weight of hexafluorobutene (Dupont, trade name FEA-1100), 30 parts by weight of polyether polyol 4110, 20 parts by weight of polyester polyol CF6320 (Jiangsu Fusheng New Material Co., Ltd.) and 1 part by weight of foam stabilizer DC3201, 12.5 parts by weight of flame retardants TCPP, and 2 parts by weight of catalyst A33 are mixed to obtain a transparent foaming composition, and then 95.5 parts by weight of isocyanate MDI (PM200) is added to the composition, to obtain a polyurethane foam material by stirring and foaming.

Samples of the polyurethane foam are prepared and cut into sheets with a cutter blade, and cells of sheet are observed with SEM (magnification 100 times). The average diameter of cells is 207 micrometres, as shown in FIG. 1.

Example 3

3 parts by weight of the compound B-1 as foaming agent prepared by above example B-1, 2 parts by weight of the compound B-2 as foaming agent prepared by above example B-2, 4 parts by weight of hexafluorobutene (Dupont, trade name FEA-1100) as foaming agent, 30 parts by weight of polyether polyol 4110, 20 parts by weight of polyester polyol CF6320 (Jiangsu Fusheng New Material Co., Ltd.) and 1 part by weight of foam stabilizer DC3201, 12.5 parts by weight of flame retardant TCPP, and 2 parts by weight of catalyst A33 are mixed to obtain a transparent foaming composition, and then 95.5 parts by weight of isocyanate MDI (PM200) is added to the composition, to obtain a polyurethane foam material by stirring and foaming.

Samples of the polyurethane foam are prepared and cut into sheets with a cutter blade, and cells of sheet are observed with SEM (magnification 100 times). The average diameter of cells is 209 micrometre.

Example 4

3 parts by weight of the compound B-2 as foaming agent prepared by above example B-2, 2 parts by weight of the compound C-2 as foaming agent prepared by above example C-2, 2 parts by weight of the compound D-1 as foaming agent prepared by above example D-1, 2 parts by weight of hexafluorobutene (Dupont, trade name FEA-1100) as foaming agent, 50 parts by weight of polyether polyol 4110 (BEFAR GROUP CO., LTD., BingZhou, China), 1 part by weight of foam stabilizer DC3201 (Air Products and Chemicals, Inc., America), 12.5 parts by weight of flame retardant TCPP (Jiangsu Yoke Chemical Co., Ltd., China), and 2 parts by weight of catalyst A33 (33LV, Air Products and Chemicals, Inc., America) are mixed to obtain a transparent foaming composition, and then 95.5 parts by weight of isocyanate MDI (PM200, WANHUA CHEMICAL GROUP CO., LTD.) is added to the composition, to obtain a polyurethane foam material by stirring and foaming.

Comparative Example 1

The example 1 is repeated except that only 9 parts by weight of hexafluorobutene is used as foaming agent.

Comparative Example 2

The example 2 is repeated except that only 9 parts by weight of compound B-1 prepared by above example B-1 is used as foaming agent.

TABLE 1 properties of polyurethane foams

| Ex. No | Foaming agent | Foam density $Kg/m^3$ | Coefficient of heat conductivity at normal temperature w/m · k (10° C.) | Compression strength Kpa | Shrinkage ratio % | Coefficient of heat conductivity at cryogenic temperature w/m · k (−160° C.) |
|---|---|---|---|---|---|---|
| 1 | A-1 and hexafluorobutene | 35.23 | 0.01835 | 184.2 Kpa | <0.2% | 0.010 |
| 2 | B-1 and hexafluorobutene | 35.01 | 0.01837 | 175.1 Kpa | <0.2% | 0.010 |
| 3 | B-1, B-2 and hexafluorobutene | 36.77 | 0.01860 | 175.1 Kpa | <0.2% | 0.0101 |
| 4 | B-2, C-2, D1 and hexafluorobutene | 36.06 | 0.01890 | 175.1 Kpa | <0.3% | 0.0102 |
| Comp. Ex. 1 | hexafluorobutene | 35.47 | 0.02010 | 175.1 Kpa | 2.5% | 0.012 |
| Comp. Ex. 2 | B-1 | 35.62 | 0.01950 | 175.1 Kpa | 0.8% | 0.011 |

Note:
the tested data in above tables are obtained by testing on the foam specimens prepared by using conventional foaming box and self-made foaming mold, wherein the foam specimens are free-rised foam specimens by hand making.

The shrinkage ratio (dimensional change ratio) is tested according to China National Standards GB/T 8811-2008.

It can be clearly seen from the data in Table 1 that the combination of the alkanolamine salt mixture (MAA) and hexafluorobutene can reduce the thermal conductivity at normal temperature, compared with Comparative Example 1. In addition, the dimensional stability of the foam material is significantly improved.

The product performance of the present invention is particularly outstanding for thermal conductivity under cryogenic condition (−160° C.). The thermal conductivity w/m·k (−160° C.) under cryogenic cooling is measured using TA company's thermal conductivity meter FOX200 LT (EKO). Test standard: ASTM-C518 (or ISO-8301). Sample size and thickness: 200 mm×200 mm, 0~50 mm.

In addition, under cryogenic cooling (−160° C.), the shrinkage rate of the foam product of Example 1 of the present invention was low by visual inspection. According to GB/T29046, the dimensional stability of the foam product of Example 1 under cryogenic cooling (−160° C.) is 0.98%, and the dimensional stability at 100° C. is 0.72%. In contrast, the foam product of Comparative Example 1 was very seriously deformed, with a shrinkage of almost 40%.

Part II: A Fifth Embodiment According to the Invention

For the high-pressure polyurethane foaming machine used in the examples, for example, a high-pressure polyurethane foaming machine manufactured by Wenzhou Zecheng Electromechanical Equipment Co., Ltd. or a GZ (Y) series high-pressure polyurethane foaming machine manufactured by Yanjin Jinlong Polyurethane Thermal Insulation Equipment Co., Ltd. can be used. For the high-pressure polyurethane spray-coating machine used in the examples, for example, QD120, QD220, or QD320 type high-pressure polyurethane spraying machine manufactured by Jinan Guozhen Machinery Equipment Co., Ltd. or a REACTOR H-VR type high-pressure polyurethane spraying machine manufactured by American Graco Company can be used.

Example 1A 40 parts by weight of polyether polyol SA460 (BEFAR GROUP CO., LTD, BingZhou, Shandong, China), 10 parts by weight of tolylenediamine-initiated polyether (Shandong Blue Star DongDa Chemical Co, Ltd.), 5 parts by weight of ethylamine (i.e, organic amine), 1 part by weight of water, 1 part by weight of foam stabilizer DC3201 (Air Products and Chemicals, Inc., America), 1 part by weight of aqueous ammonia (27% concentration), 12.5 parts by weight of flame retardant TCPP (Jiangsu Yoke Chemical Co., Ltd., China), and 2 parts by weight of catalyst A33 (33LV, Air Products and Chemicals, Inc., America) are mixed to obtain a transparent foaming composition, that is "white material" or called combined polyether polyols. Then, the "white material" is delivered into a pressure vessel for storage.

80 parts of isocyanate MDI (PM200, Wanhua Chemical Group Co., Ltd., Yantai) is used as the isocyanate raw material (i.e., "black material") to be stored in a pressure vessel.

Supercritical $CO_2$ is introduced into the pressure vessel containing the white material, and maintained at a pressure of 3.5 MPa, a temperature of 30° C., and a rotational speed of 200 rpm for ten minutes to allow the supercritical fluid to fully penetrate and diffuse in the polymer material to form a polymer-supercritical fluid homogeneous system. The continuous decrease in pressure is observed, indicating that the white material has a good absorption effect on carbon dioxide. Then, the white material and the black material are respectively transported from the pressure container storing the white material and the pressure container storing the black material to the supercritical $CO_2$ reactor for mixing, and the resulting mixture is decompressed through a pressure relief valve and discharged for casting foaming to obtain a polyurethane foam.

Example 2A 40 parts by weight of polyether polyol 2010 (BEFAR GROUP CO., LTD, BingZhou, Shandong, China), 10 parts by weight of tolylenediamine-initiated polyether (Shandong Blue Star DongDa Chemical Co, Ltd.), 6.5 parts by weight of monopropanolamine (i.e, organic amine), 1 part by weight of water, 1 part by weight of foam stabilizer DC3201 (Air Products and Chemicals, Inc., America), 1 part by weight of aqueous ammonia (27% concentration), 12.5 parts by weight of flame retardant TCPP (Jiangsu Yoke Chemical Co., Ltd., China), and 2 parts by weight of catalyst A33 (33LV, Air Products and Chemicals, Inc., America) are mixed to obtain a transparent foaming composition, that is "white material" or called combined polyether polyols. Then, the "white material" is delivered into a pressure vessel for storage.

80 parts of isocyanate MDI (PM200, Wanhua Chemical Group Co., Ltd., Yantai) is used as the isocyanate raw material (ie, "black material") to be stored in a pressure vessel.

Supercritical $CO_2$ was introduced into the pressure vessel containing the white material, and maintained at a pressure of 3.5 MPa, a temperature of 30° C., and a rotation speed of 200 rpm for ten minutes to allow the supercritical fluid to fully penetrate and diffuse into the polymer material to form a polymer-supercritical fluid homogeneous system. The continuous decrease in pressure is observed, indicating that the white material has a good absorption effect on carbon dioxide. Then, the white material and the black material are respectively transported from the pressure container storing the white material and the pressure container storing the black material to the supercritical $CO_2$ reactor for mixing, and the resulting mixture is decompressed through a pressure relief valve and discharged for casting foaming to obtain a polyurethane foam.

Example 3A

Supercritical $CO_2$ is introduced into both the white material and black material.

40 parts by weight of polyether polyol SA460 (BEFAR GROUP CO., LTD., BingZhou, Shandong, China), 10 parts by weight of tolylenediamine-initiated polyether (Shandong Blue Star DongDa Chemical Co, Ltd.), 6 parts by weight of monoethanolamine (i.e, organic amine), 1 part by weight of water, 1 part by weight of foam stabilizer DC3201 (Air Products and Chemicals, Inc., America), 0.3 part by weight of N,N-dimethyl cyclohexylamine (Air Products and Chemicals), 1.5 parts by weight of potassium octoate, 1 part by weight of aqueous ammonia (27% concentration), 12 parts by weight of flame retardant TCEP (tri-chloroethyl phosphate), and 2 parts by weight of flame retardants DMMP (dimethyl methylphosphonate) are mixed to obtain a transparent foaming composition, that is "white material" or called combined polyether polyols.

80 parts of isocyanate MDI (PM200, Wanhua Chemical Group Co., Ltd., Yantai) is used as the isocyanate raw material, that is, "black material".

A high-pressure polyurethane foaming machine is used as the foaming equipment.

The white material (that is, the combined polyether polyols) and the black material (that is, the isocyanate raw material) are respectively pressurized and injected into corresponding storage containers of the high-pressure polyurethane foaming machine, and the pressure is adjusted to 3.5 MPa.

The heater switch of the high-pressure polyurethane foaming machine is turned on, and the heating temperature is set to 30° C. and the heat preservation mode is set up.

Supercritical $CO_2$ is introduced into the pressure vessel containing the white material, and maintained at a pressure of 3.5 MPa, a temperature of 30° C., and a rotation speed of 200 rpm for ten minutes to allow the supercritical fluid to fully penetrate and diffuse into the polymer material to form a polymer-supercritical fluid homogeneous system. The continuous decrease in pressure is observed, indicating that the white material has a good absorption effect on carbon dioxide. At the same time, supercritical $CO_2$ is introduced into the pressure vessel containing the black material, and maintained at a pressure of 3.5 MPa, a temperature of 30° C., and a rotation speed of 200 rpm for ten minutes. Then, two gear pumps are used respectively to transport the white material and black material from the pressure container storing the white material (polyether polyol) and the pressure container storing the black material (isocyanate) to the spray gun mixing chamber for rapid mixing, and the spray gun switch is turn on to perform spraying and foaming, thereby obtaining a polyurethane foam.

Example 4A 40 parts by weight of polyether polyol SU380 (BEFAR GROUP CO., LTD., BingZhou, Shandong, China), 10 parts by weight of tolylenediamine-initiated polyether (Shandong Blue Star DongDa Chemical Co, Ltd.), 5 parts by weight of monoethanolamine (i.e, organic amine), 2 parts by weight of di(ethanolamine) carbonate (i.e, organic amine), 1 part by weight of water, 1 part by weight of foam stabilizer DC3201 (Air Products and Chemicals, Inc., America), 0.3 part by weight of N,N-dimethyl cyclohexylamine (Air Products and Chemicals), 1.5 parts by weight of potassium octoate, 1 part by weight of aqueous ammonia (27% concentration), 12 parts by weight of flame retardant TCEP (tri-chloroethyl phosphate), and 2 parts by weight of flame retardant DMMP (dimethyl methylphosphonate) are mixed to obtain a transparent foaming composition, that is "white material" or called combined polyether polyols.

80 parts of isocyanate MDI (PM200, Wanhua Chemical Group Co., Ltd., Yantai) is used as the isocyanate raw material, that is, "black material".

A high pressure polyurethane spraying machine is used as foaming equipment.

The white material (that is, the combined polyether polyols) and the black material (that is, the isocyanate raw material) are respectively pressurized and injected into corresponding storage containers of the high-pressure polyurethane foaming machine, and the pressure is adjusted to 3.2 MPa.

The heater switch of the high-pressure polyurethane foaming machine is turned, the heating temperature is set to 20° C., and the heat preservation mode is set up.

Supercritical $CO_2$ is introduced into the pressure vessel containing the white material, and maintained at a pressure of 3.5 MPa, a temperature of 30° C., and a rotation speed of 200 rpm for ten minutes to allow the supercritical fluid to fully penetrate and diffuse into the polymer material to form a polymer-supercritical fluid homogeneous system. The continuous decrease in pressure is observed, indicating that the white material has a good absorption effect on carbon dioxide. Then two gear pumps are used respectively to transport the white and black materials from the pressure container storing the white material (polyether polyol) and the pressure container storing the black material (isocyanate) to the spray gun mixing chamber for rapid mixing, and the spray gun switch is turned on to perform casting foaming, thereby obtaining a polyurethane foam.

Example 5A

Example 4A was repeated, except that 1 part by weight of di(ethanolamine) carbonate is used instead of 2 parts by weight of di(ethanolamine) carbonate, and 2 parts by weight of hexafluorobutene is further added to the white material.

Example 6A

Example 2A is repeated, except that supercritical $CO_2$ is not introduced into the white material, and only supercritical $CO_2$ is introduced into the pressure vessel containing the black material, and maintained for ten minutes at a pressure of 3.5 MPa, a temperature of 30° C., and a rotation speed of 200 rpm, thereby obtaining a polyurethane foam.

Comparative Example 1A

Example 1A is repeated, except that ethylamine is not added to the white material.

Comparative Example 2A

Example 4A is repeated, except that no organic amines (ie, monoethanolamine and di(ethanolamine) carbonate) are added to the white material.

TABLE 1

| | Example 1A | Example 2A | Example 3A | Example 4A | Example 5A | Comp. Ex. 1A | Comp. Ex. 2A |
|---|---|---|---|---|---|---|---|
| Foam density Kg/m$^3$ | 37.78 | 36.54 | 36.34 | 36.21 | 35.62 | 43.10 | 41.02 |
| Average cell size (micron) | 202 | 208 | 207 | 208 | 210 | 153 | 155 |
| Coefficient of heat conductivity w/m · k (10° C.) | 0.01891 | 0.01883 | 0.01875 | 0.01856 | 0.01836 | 0.02011 | 0.02005 |
| Shrinkage % (25° C., 5 months) | 0.78% | <0.2% | <0.2% | <0.2% | <0.2% | 2.8% | 3.2% |
| Coefficient of heat conductivity under cryogenic cooling w/m · k (−160° C.) | 0.0110 | 0.0103 | 0.0102 | 0.0102 | 0.0100 | 0.0122 | 0.0121 |
| Shrinkage % under cryogenic cooling (−160° C.) | 6% | 4% | 2.5% | 1.2% | 1% | 40% | 38% |

The shrinkage rate (dimension change rate) is measured according to the Chinese National Standard GB/T 8811-2008, but the storage time is 5 months.

For thermal conductivity w/m·k (−160° C.) under cryogenic cooling, it is measured using TA company's thermal conductivity meter FOX200 LT (EKO). Test standard: ASTM-C518 (or ISO-8301). Sample sizes and thickness: 200 mm×200 mm, 0~50 mm.

Figure 2:
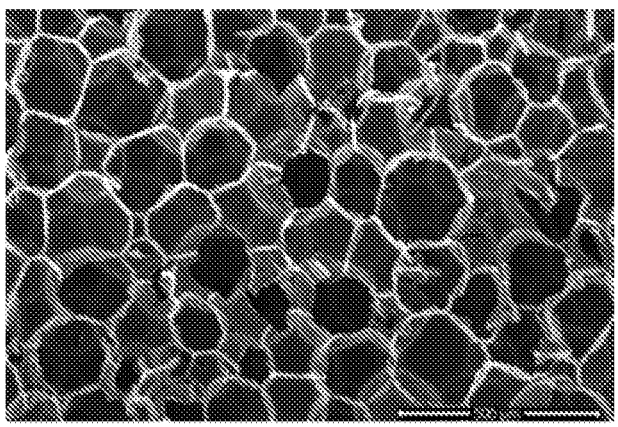
FIG. 2 is a scanning electron microscope (SEM) photograph of the foam of example 1A.
Figure 3:
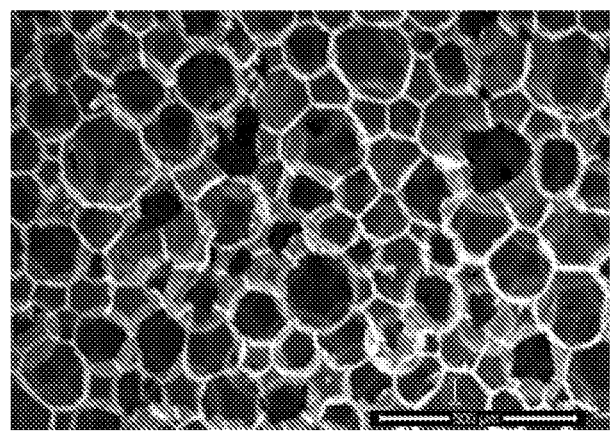
FIG. 3 is a scanning electron microscope (SEM) photograph of the foam of comparative example 1A.

As can be seen from FIG. 2 and FIG. 3, compared with Comparative Example 1A (FIG. 3), the foam (FIG. 2) of Example 1A of the present invention has more uniform cell size, and the cell size is larger. It is shown that the absorption amount of carbon dioxide in the present invention is larger, and carbon dioxide is more uniformly distributed in the white material.

Part III: A Sixth Embodiment According to the Invention

With respect to the measuring method of the content of various alkanolamines (such as monoethanolamine, diethanolamine, triethanolamine, monopropanolamine, dipropanolamine or tripropanolamine) in the alkanolamine salt compounds, gas chromatography can be used. The gas chromatograph is fitted with hydrogen flame ionization detector (FID), and the mass concentration of the compound of the general formula (I) is about 10 mg/mL, used as a standard solution. The gas phase chromatography conditions: HP-5 adsorption capillary column (30 m*0.32 mm i.d.*0.25 μm, 5% phenyl methyl-siloxane); the column temperature is regulated by temperature programming, its initial temperature is set at 80° C. and is maintained for 3 min., and then the column temperature is increased to 250° C. at the heating rate of 25° C./min and maintained for 5 min.; wherein: the injection port temperature is 250° C.; the detector temperature is 260° C.; the carrier gas is high purity nitrogen gas, and its flow rate is 1.5 mL/min.; the combustible gas is hydrogen gas, and its flow rate is 30 mL/min.; the combustion-supporting gas is air, and its flow rate is 300 mL/min.; the makeup gas is nitrogen gas, and its flow rate is 25 mL/min.; the manner of sample injection is split stream sampling, the split ratio: 30:1, and the sample size for it is 1 μL.

Preparation Example 1B

The First Stage:

14 kg of ammonium carbamate (molecular weight 78.07), and 17 kg of water are charged into a stainless steel autoclave equipped with cooling water jacket (hereinafter referred to reactor, for short), a stirrer is started to make ammonium carbamate dissolve, and the reactor is purged with nitrogen gas, and then the reactor is closed and the stirrer is started again. 19 kg of propylene oxide (molecular weight 58.08, boiling point 34° C.) in total is fed into the reactor, wherein the charging rate of propylene oxide should be controlled so as to keep the pressure in the reactor to a pressure no more than 0.6 MPa, the reaction system is heated up slowly with continual agitation, and the reaction system is conducted for 13 hours at the controlled reaction temperature below 65° C. After the completion of the reaction, the temperature of the reaction system is lowered slowly to 45° C.; the vacuum is released and the temperature of the reaction system is lowered slowly to below 40° C., and the reaction product is discharged to obtain compound A1-MAA1 (i.e., alkanolamine salt mixture MAA). Its viscosity is about 320 centipoise, pH=9, and the decomposition temperature of compound A1-MAA1 is in a range of 59-61° C. By the gas chromatographic analysis, the mole ratio of monopropanol amine to dipropanol amine in the compound A1-MAA1 is 1:0.17. The compound A1-MAA1 contains about 67 wt % of both salts of the monopropanol amine and dipropanol amine. A sample of 5 kg compound A1-MAA1 is heated at 66° C. for 5 minutes to decompose and release carbon dioxide to obtain a residue. The residue is then rectified with a small laboratory rectification column, and 1.65 kg of water is separated. The water content of the compound A1-MAA1 is measured to be 33 wt %.

The Second Stage:

11 kg of ammonium carbamate (molecular weight 78.07), and 25 kg of compound A1-MAA1 obtained in the first stage are charged into a stainless steel autoclave equipped with cooling water jacket, a stirrer is started such that ammonium carbamate is dispersed and dissolved in the compound A1-MAA1 used as dispersion medium, the reactor is purged with nitrogen gas, and then the reactor is closed and the stirrer is started again. 14 kg of propylene oxide (molecular weight 58.08, boiling point 34° C.) in total is fed into the reactor, wherein the charging rate of propylene oxide should be controlled so as to keep the pressure in the reactor to a pressure no more than 0.6 MPa, the reaction system is heated up slowly with continual agitation, and the reaction is conducted for 15 hours at the reaction temperature controlled to below 65° C. After the completion of the reaction, the temperature of the reaction system is lowered slowly to 45° C., and then the vacuum is released and the temperature of the reaction system is lowered slowly to below 40° C., and the reaction product is discharged to obtain compound A1-MAA2 (i.e., alkanolamine salt mixture MAA). Its viscosity is about 430 centipoise, pH=9, and the decomposition temperature of the compound A1-MAA2 is in a range of 59-61° C. By the gas chromatographic analysis, the mole ratio of monopropanol amine to dipropanol amine in the compound A1-MAA2 is 1:0.35. The compound A1-MAA2 contains about 83 wt % of both salts of the monopropanol amine and dipropanol amine. A sample of 5 kg of the compound A1-MAA2 is heated at 66° C. for 5 minutes to decompose and release carbon dioxide, and a residue is obtained. The residue is then rectified with a small laboratory rectification column, 0.85 kg of water is separated, and the water content of the compound A1-MAA2 is measured to be 17 wt %.

The Third Stage:

11 kg of ammonium carbamate (molecular weight 78.07) and 25 kg of the compound A1-MAA2 obtained in the second stage are charged into a stainless steel autoclave equipped with cooling water jacket, the stirrer is started such that ammonium carbamate is dispersed and dissolved in the compound A1-MAA2 used as dispersion medium, the reactor is purged with nitrogen gas, and then the reactor is closed and the stirrer is started again. 14 kg of propylene oxide (molecular weight 58.08, boiling point 34° C.) in total is fed into the reactor, wherein the charging rate of propylene oxide should be controlled so as to keep the pressure in the reactor to a pressure no more than 0.6 MPa, the reaction system is heated up slowly with continual agitation, and the reaction is conducted for 15 hours at the reaction temperature controlled to below 65° C. After the completion of the reaction, the temperature of the reaction system is lowered slowly to below 45° C., the vacuum is released and the temperature of the reaction system is lowered slowly to below 40° C., and the reaction product is discharged to obtain compound A1-MAA3 (i.e., alkanolamine salt mixture MAA). Its viscosity is about 730 centipoise, pH=9, and the decomposition temperature of compound A1-MAA3 is in a range of 59-61° C. By the gas chromatographic analysis, the mole ratio of monopropanol amine to dipropanol amine in the compound A1-MAA3 is 1:0.58. The compound A1-MAA3 contains about 91 wt % of both salts of the monopropanol amine and dipropanol amine. A 5 kg sample of compound A1-MAA3 is heated at 66° C. for 5 minutes, and is decomposed to release carbon dioxide and to obtain a residue. The residue is then rectified with a small laboratory rectification column, 0.425 kg of water is separated, and the water content of the compound A1-MAA3 is measured to be 8.5 wt %.

The Fourth Stage:

11 kg of ammonium carbamate (molecular weight 78.07), and 25 kg of the compound A1-MAA3 obtained in the third stage are charged into a stainless steel autoclave equipped with cooling water jacket, a stirrer is started such that ammonium carbamate is dispersed and dissolved in the compound A1-MAA3 used as dispersion medium, the reactor is purged with nitrogen gas, and then the reactor is closed and the stirrer is started again. 14 kg of propylene oxide (molecular weight 58.08, boiling point 34° C.) in total is fed into the reactor, wherein the charging rate of propylene oxide should be controlled so as to keep the pressure in the reactor to a pressure no more than 0.6 MPa, the reaction system is heated up slowly with continual agitation, and the reaction is conducted for 15 hours at the reaction temperature controlled to below 65° C. After the completion of the reaction, the temperature of the reaction system is lowered slowly to 45° C., the vacuum is released and the temperature of the reaction system is lowered slowly to below 40° C., and the reaction product is discharged to obtain compound A1-MAA4 (i.e., alkanolamine salt mixture MAA). Its viscosity is about 810 centipoise, pH=9, and the decomposition temperature of compound A1-MAA4 is in a range of 59-61° C. By the gas chromatographic analysis, the mole ratio of monopropanol amine to dipropanol amine in the compound A1-MAA4 is 1:0.82. The compound A1-MAA4 contains about 95.7 wt % of both salts of the monopropanol amine and dipropanol amine. A 5 kg sample of the compound A1-MAA4 is heated at 66° C. for 5 minutes, and is decomposed to release carbon dioxide, and a residue is obtained. The residue is then rectified with a small laboratory rectification column, 0.215 kg of water is separated, and the water content of compound A1-MAA4 is measured to be 4.3 wt %.

Preparation Example 2B

The First Stage:

16 kg of ammonium carbonate (molecular weight 96) and 16 kg of water are charged to a reactor and stirred to dissolve ammonium carbonate, the reactor is purged with nitrogen gas, and then 28 kg of propylene oxide is added to the reactor and stirred. The resultant reaction system is heated up slowly with continual agitation, and the reaction is carried out for 15 hours at a temperature controlled to below 60° C. and the pressure controlled to no more than 0.6 MPa. After the reaction is finished, the temperature of the reaction system is reduced to 40° C., the vacuum is released, and the resulting product is discharged, so as to obtain compound A2-MAA1 (i.e., alkanolamine salt mixture MAA). Its viscosity is about 290 centipoise, pH=9, and the decomposition temperature of the compound A2-MAA1 is in a range of 59-61° C. By the gas chromatographic analysis, the mole ratio of monopropanol amine to dipropanol amine in the compound A2-MAA1 is 1:0.28. The compound A2-MAA1 contains about 73.3 wt % of both salts of the monopropanol amine and dipropanol amine. A sample of 5 kg compound A2-MAA1 is heated at 66° C. for 5 minutes to decompose and release carbon dioxide, thereby obtaining a residue. The residue is then rectified with a small laboratory rectification column, and 1.33 kg of water is separated. The water content of the compound A1-MAA1 is measured to be 26.6 wt %.

The Second Stage:

9 kg of ammonium carbonate (molecular weight 96) and 25 kg of the compound A2-MAA1 obtained in the first stage are charged into a stainless steel autoclave equipped with cooling water jacket, a stirrer is started such that ammonium carbonate is dispersed and dissolved in the compound A2-MAA1 used as dispersion medium, the reactor is purged with nitrogen gas, and then the reactor is closed and the stirrer is started again. 16 kg of propylene oxide (molecular weight 58.08, boiling point 34° C.) in total is fed into the reactor, wherein the charging rate of propylene oxide should be controlled so as to keep the pressure in the reactor no more than 0.6 MPa, the reaction system is heated up slowly with continual agitation, and the reaction is carried out for 15 hours at the reaction temperature controlled to below 65° C. After the completion of the reaction, the temperature of the reaction system is lowered slowly to below 45° C., the vacuum is released and the temperature of the reaction system is lowered slowly to below 40° C., and the reaction product is discharged to obtain compound A2-MAA2 (i.e., alkanolamine salt mixture MAA). Its viscosity is about 430 centipoise, pH=9, and the decomposition temperature of the compound A2-MAA2 is in a range of 59-61° C. By the gas chromatographic analysis, the mole ratio of monopropanol amine to dipropanol amine in the compound A2-MAA2 is 1:0.41. The compound A2-MAA2 contains about 83 wt % of both salts of the monopropanol amine and dipropanol amine. A 5 kg sample of the compound A2-MAA2 is heated at 66° C. for 5 minutes, and is decomposed to release carbon dioxide, thereby obtaining a residue. The residue is then rectified with a small laboratory rectification column, and 0.666 kg of water is separated. The water content of the compound A2-MAA2 is measured to be 13.3 wt %.

The Third Stage:

9 kg of ammonium carbonate (molecular weight 96) and 25 kg of the compound A2-MAA2 obtained in the second stage are charged into a stainless steel autoclave equipped with cooling water jacket, a stirrer is started such that ammonium carbonate is dispersed and dissolved in the compound A2-MAA2 used as dispersion medium, the reactor is purged with nitrogen gas, and then the reactor is closed and the stirrer is started again. 16 kg of propylene oxide (molecular weight 58.08, boiling point 34° C.) in total is fed into the reactor, wherein the charging rate of propylene oxide should be controlled so as to keep the pressure in the reactor no more than 0.6 MPa, the reaction system is heated up slowly with continual agitation, and the reaction is carried out for 15 hours at the reaction temperature controlled to below 65° C. After the completion of the reaction, the temperature of the reaction system is lowered slowly to 45° C., the vacuum is released and the temperature of the reaction system is lowered slowly to below 40° C., and the reaction product is discharged to obtain compound A2-MAA3 (i.e., alkanolamine salt mixture MAA). Its viscosity is about 540 centipoise, pH=9, and the decomposition temperature of the compound A2-MAA3 is in a range of 59-61° C. By the gas chromatographic analysis, the mole ratio of monopropanol amine to dipropanol amine in the compound A2-MAA3 is 1:0.52. The compound A2-MAA3 contains about 93.3 wt % of both salts of the monopropanol amine and dipropanol amine. A 5 kg sample of the compound A2-MAA3 is heated at 66° C. for 5 minutes, and is decomposed to release carbon dioxide and obtain a residue. The residue is then rectified with a small laboratory rectification column, 0.333 kg of water is separated, and the water content of the compound A2-MAA3 is measured to be 6.66 wt %.

APPLICATION EXAMPLES

Example 1B 5 parts by weight of the compounds A1-MAA4 (water content 4.3 wt %) as foaming agent prepared by above example 1B, 4 parts by weight of hexafluorobutene (Dupont, trade name FEA-1100), 50 parts by weight of polyether polyol 4110 (BEFAR GROUP CO., LTD, BingZhou, Shandong, China), 1 part by weight of foam stabilizer DC3201 (Air Products and Chemicals, Inc., America), 12.5 parts by weight of flame retardant TCPP (Jiangsu Yoke Chemical Co., Ltd., China), and 2 parts by weight of catalyst A33 (33LV, Air Products and Chemicals, Inc., America) are mixed to obtain a transparent foaming composition, thereto 95.5 parts by weight of isocyanate MDI (PM200, WANHUA CHEMICAL GROUP CO., LTD.) is added, and then a polyurethane foam material is obtained by stirring and foaming.

Example 2B 3 parts by weight of the compounds A2-MAA3 (water content 6.66 wt %) as foaming agent prepared by above example 2B, 6 parts by weight of hexafluorobutene (Dupont, trade name FEA-1100), 30 parts by weight of polyether polyol 4110, 20 parts by weight of polyester polyol CF6320 (Jiangsu Fusheng New Material Co., Ltd.), 1 part by weight of foam stabilizer DC3201, 12.5 parts by weight of flame retardant TCPP, and 2 parts by weight of catalyst A33 are mixed to obtain a transparent foaming composition, thereto 95.5 parts by weight of isocyanate MDI (PM200) is added, and then a polyurethane foam material is obtained by stirring and foaming.

Comparative Example 1B

The example 1B is repeated except that only 9 parts by weight of hexafluorobutene is used as foaming agent.

TABLE 1 properties of polyurethane foams

| Ex. No | Foaming agent | Foam density Kg/m$^3$ | Coefficient of heat conductivity at normal temperature w/m · k (10° C.) | Compression strength Kpa | Shrinkage ratio % | Coefficient of heat conductivity at cryogenic temperature w/m · k (−160° C.) |
|---|---|---|---|---|---|---|
| 1B | A1-MAA4 and hexafluorobutene | 35.67 | 0.01842 | 189.7 Kpa | <0.2% | 0.010 |
| 2B | A2-MAA3 and hexafluorobutene | 35.44 | 0.01835 | 187.2 Kpa | <0.2% | 0.010 |
| Comp. Ex. 1B | hexafluorobutene | 35.45 | 0.02010 | 171.2 Kpa | 2.7% | 0.012 |

Note:
the tested data in above tables is obtained by testing on the foam specimens prepared by using conventional foaming box and self-made foaming mold, wherein the foam specimens are free-rised foam specimens by hand making.

The shrinkage ratio (dimensional change ratio) is tested according to China National Standards GB/T 8811-2008.

From the data in Table 1, it can be clearly seen that the combination of low water content alkanolamine salt mixture (MAA) with hexafluorobutene can improve the compressive strength of foam, and also can reduce the thermal conductivity of the foam at room temperature, compared with Comparative Example 1. In addition, the dimensional stability of the foam material is significantly improved.

The product performance of the present invention is particularly outstanding with respect to thermal conductivity of foam under cryogenic (−160° C.). For thermal conductivity w/m·k (−160° C.) under cryogenic cooling, TA company's thermal conductivity meter FOX200 LT (EKO) is used. Test standard: ASTM-C518 (or ISO-8301). Sample size and thickness: 200 mm×200 mm, 0~50 mm.

Additionally, under deep cooling (−160° C.), the shrinkage rate of the product of Example 1B of the present invention is relatively low by visual inspection. According to GB/T29046, the dimensional stability of the product of Example 1B under deep cold (−160° C.) is 0.97%, and the dimensional stability at 100° C. is 0.75%. The product of Comparative Example 1B was very seriously deformed, with a shrinkage of almost 45%.

The invention claimed is:
1. A composite foaming agent, comprising:
1) hexafluorobutene; and
2) an alkanolamine salt mixture (MAA),
wherein the alkanolamine salt mixture (MAA) comprises organic alkanolamine salt compounds, and the organic alkanolamine salt compounds is an organic alkanolamine salt compound having following general formula (I):

$$A^{n-}[B^{m+}]_p \qquad (I)$$

in the above formula, $A^{n-}$ is $CO_3^{2-}$; wherein n=2, m=1, and p=2;
$B^{m+}$ comprises: one or more organic amine (B) cation(s) having one $-{}^+NR^3R^4H$ group;
wherein, $R^3$ and $R^4$ is independently chosen from: H, or R;
provided that: the compound of the general formula (I) has at least one R group(s) linked to N atom, and the alkanolamine salt mixture (MAA) contain(s) 50-99 wt % of monoalkanolamine salt or dialkanolamine salt, based on total weight of the alkanolamine salt mixture (MAA);
wherein the R group is $H[OCH(R_{1a})CH(R_{2a})]-$;
wherein $R_{1a}$, $R_{2a}$ each independently is selected from the following groups: H, $C_1$-$C_7$ aliphatic hydrocarbyl group optionally substituted by hydroxyl or amino or halogen, and $C_3$-$C_7$ cycloaliphatic hydrocarbyl group optionally substituted by hydroxyl or amino or halogen;
wherein water content in the alkanolamine salt mixture (MAA) is from more than 0 wt % to 40 wt %, and said one or more organic amine cation(s) (B) is/are organic amine cation(s) having 2-20 carbon atoms;
wherein the weight ratio of hexafluorobutene to alkanolamine salt mixture (MAA) in the composite foaming agent is 0.4-5:1.

2. The composite foaming agent according to claim 1, wherein monoalkanolamine is monoethanolamine and/or monopropanolamine; Dialkanolamine is diethanolamine, ethanol propanol amine and/or dipropanolamine.

3. The composite foaming agent according to claim 1, wherein:

$H[OCH(R_{1a})CH(R_{2a})]$— is $H(OCH_2CH_2)$—, $H(OCH_2CH(CH_3))$—, $H(OCH(CH_3)CH_2)$—, and the weight ratio of hexafluorobutene to alkanolamine salt mixture (MAA) in the composite foaming agent is 0.5-4:1.

4. The composite foaming agent according to claim 1, wherein the weight ratio of hexafluorobutene to alkanolamine salt mixture (MAA) in the composite foaming agent is 0.7-3:1.

5. The composite foaming agent according to claim 1, wherein the weight ratio of hexafluorobutene to alkanolamine salt mixture (MAA) in the composite foaming agent is 0.7-2:1.

6. The composite foaming agent according to claim 1, wherein the weight ratio of hexafluorobutene to alkanolamine salt mixture (MAA) in the composite foaming agent is 0.7-1.3:1.

7. The composite foaming agent according to claim 1, wherein the water content in the alkanolamine salt mixture (MAA) is 5-35 wt %, and the alkanolamine salt mixture (MAA) contains 60-98 wt % of monoalkanolamine salt or dialkanolamine salt; and the pH of the alkanolamine salt mixture (MAA) is 7.5-10.

8. The composite foaming agent according to claim 1, wherein the water content in the alkanolamine salt mixture (MAA) is 10-30 wt %, and the alkanolamine salt mixture (MAA) contains 70-97 wt % of monoalkanolamine salt or dialkanolamine salt; and the pH of the alkanolamine salt mixture (MAA) is 7.8-9.5.

9. The composite foaming agent according to claim 1, wherein the water content in the alkanolamine salt mixture (MAA) is 15-25 wt %, and the alkanolamine salt mixture (MAA) contains 80-96 wt % of monoalkanolamine salt or dialkanolamine salt; and the pH of the alkanolamine salt mixture (MAA) is 8-9.

10. The composite foaming agent according to claim 1, wherein: in the alkanolamine salt mixture (MAA), the total content of the compound of the general formula (I) and water is 70-100%, based on the total weight of alkanolamine salt mixture (MAA).

11. The composite foaming agent according to claim 10, wherein: in the alkanolamine salt mixture (MAA), the total content of the compound of the general formula (I) and water is 80-99.5%, based on the total weight of alkanolamine salt mixture (MAA).

12. The composite foaming agent according to claim 10, wherein: in the alkanolamine salt mixture (MAA), the total content of the compound of the general formula (I) and water is 85-99.0%, based on the total weight of alkanolamine salt mixture (MAA).

13. The composite foaming agent according to claim 1, wherein the alkanolamine salt mixture (MAA) is formed by the reaction of a first raw material and a second raw material in the presence of water; wherein the first raw material is one or more selected from the following compounds:

$(NH_4)_2CO_3$, or organic amine compound (M) carbonate;
wherein the organic amine compound (M) is an organic amine compound selected from following compounds:
$C_1$ hydrocarbyl amines;
Di-($C_1$ hydrocarbyl) amines;
$C_2$-$C_{14}$ hydrocarbylene diamines;
$C_4$-$C_{16}$ polyalkylene polyamines;
$C_3$-$C_{18}$ organic triamines having three primary amine groups or $C_5$-$C_{18}$ organic tetramines having four primary amine groups; or
$C_2$-$C_{10}$ alkanolamines;
the second material is one or more selected from following epoxides:

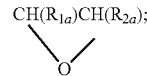

wherein $R_{1a}$, $R_{2a}$ each independently is selected from the following groups: H, $C_1$-$C_7$ aliphatic hydrocarbyl group optionally substituted by hydroxyl or amino or halogen, or $C_3$-$C_7$ cycloaliphatic hydrocarbyl group optionally substituted by hydroxyl or amino or halogen.

14. The composite foaming agent according to claim 13, wherein the amount of water is 70-200 wt %, based on the weight of the first raw material.

15. The composite foaming agent according to claim 1, wherein $R_{1a}$, $R_{2a}$ each independently is selected from the following groups: H, methyl, chloromethyl, bromomethyl, ethyl, or cyclohexyl.

16. The composite foaming agent according to claim 1, wherein the mass content of alkali metals and alkaline earth metals in the foaming agent is 0-200 ppm.

* * * * *